(12) United States Patent
Kumar et al.

(10) Patent No.: US 7,553,448 B2
(45) Date of Patent: Jun. 30, 2009

(54) ELECTROCHEMILUMINESCENCE FLOW CELL AND FLOW CELL COMPONENTS

(75) Inventors: Sudeep M. Kumar, Gaithersburg, MD (US); Josephus Marinus Otten, Gaithersburg, MD (US); Charles Quentin Davis, Frederick, MD (US); Hans Biebuyck, Rockville, MD (US)

(73) Assignee: Bioveris Corporation, Gaithersburg, MD (US)

( * ) Notice: Subject to any disclaimer, the term of this patent is extended or adjusted under 35 U.S.C. 154(b) by 539 days.

(21) Appl. No.: 10/600,164

(22) Filed: Jun. 19, 2003

(65) Prior Publication Data

US 2004/0090168 A1 May 13, 2004

Related U.S. Application Data

(60) Provisional application No. 60/390,816, filed on Jun. 20, 2002.

(51) Int. Cl.
*G01N 21/76* (2006.01)
*C12M 3/00* (2006.01)
*G01N 21/64* (2006.01)
*G01N 33/00* (2006.01)

(52) U.S. Cl. .............. 422/52; 422/82.05; 422/82.07; 422/82.08; 422/68.1; 435/287.2; 436/172

(58) Field of Classification Search ............ 422/52
See application file for complete search history.

(56) References Cited

U.S. PATENT DOCUMENTS

| 3,583,230 A | 6/1971 | Patterson | |
|---|---|---|---|
| 3,676,784 A | 7/1972 | Le Comte | |
| 3,784,928 A * | 1/1974 | Crane | 372/33 |
| 3,816,795 A | 6/1974 | Maricle et al. | |
| 3,900,418 A * | 8/1975 | Bard et al. | 252/62.2 |
| 3,961,253 A | 6/1976 | Brych | |
| 3,984,688 A | 10/1976 | Von Bargen et al. | |
| 4,007,011 A | 2/1977 | Greaves et al. | |
| 4,132,605 A * | 1/1979 | Tench et al. | 205/787 |

(Continued)

FOREIGN PATENT DOCUMENTS

DE 197 25 190 A1 12/1998

(Continued)

OTHER PUBLICATIONS

PCT International Search Report, Dec. 31, 2003.

(Continued)

*Primary Examiner*—Jill Warden
*Assistant Examiner*—Neil Turk
(74) *Attorney, Agent, or Firm*—Foley & Lardner LLP

(57) ABSTRACT

An electrochemiluminescence cell comprising an electrode capable of inducing an electrochemiluminescence-active species to electrochemiluminesce. The electrode is preferably made of rhodium, iridium or an alloy of platinum, rhodium or iridium alloyed with an alloy material comprising a transition element. The electrode may be used as counter electrode and/or as a working electrode in the electrochemiluminescence cell. The cell preferably includes a counter electrode and a support attached to the counter electrode. The support comprises a transparent portion in optical registration with the working electrode. The counter electrode may include one or more field extending elements interposed between the transparent portion and the working electrode. The field extending element is preferably a ladder or a grid.

43 Claims, 13 Drawing Sheets

U.S. PATENT DOCUMENTS

| | | | |
|---|---|---|---|
| 4,210,724 A | 7/1980 | Sogi et al. | |
| 4,213,703 A | 7/1980 | Haunold et al. | |
| 4,280,815 A | 7/1981 | Oberhardt et al. | |
| 4,297,105 A | 10/1981 | Dube | |
| 4,303,410 A | 12/1981 | Copeland | |
| 4,431,919 A | 2/1984 | Köstlin et al. | |
| 4,443,713 A | 4/1984 | Layton | |
| 4,537,861 A | 8/1985 | Elings et al. | |
| 4,619,745 A | 10/1986 | Porta et al. | |
| 4,771,215 A | 9/1988 | Munakata et al. | |
| 4,849,340 A | 7/1989 | Oberhardt | |
| 5,061,445 A | 10/1991 | Zoski et al. | |
| 5,068,088 A | 11/1991 | Hall et al. | |
| 5,093,268 A | 3/1992 | Leventis et al. | |
| 5,112,646 A | 5/1992 | Koshi et al. | |
| 5,132,227 A | 7/1992 | Kelly | |
| 5,147,806 A | 9/1992 | Kamin et al. | |
| 5,189,549 A | 2/1993 | Leventis et al. | |
| 5,240,863 A | 8/1993 | Shibue et al. | |
| 5,247,243 A | 9/1993 | Hall et al. | |
| 5,296,191 A | 3/1994 | Hall et al. | |
| 5,298,427 A | 3/1994 | Bobbitt et al. | |
| 5,310,687 A | 5/1994 | Bard et al. | |
| 5,324,457 A * | 6/1994 | Zhang et al. | 252/700 |
| 5,429,893 A | 7/1995 | Thomas | |
| 5,451,528 A | 9/1995 | Raymoure et al. | |
| 5,466,416 A | 11/1995 | Ghaed et al. | |
| 5,500,188 A | 3/1996 | Hafeman et al. | |
| 5,538,687 A | 7/1996 | Kotzan et al. | |
| 5,541,113 A | 7/1996 | Siddigi et al. | |
| 5,589,136 A | 12/1996 | Northrup et al. | |
| 5,591,321 A * | 1/1997 | Pyke | 205/787 |
| 5,624,637 A | 4/1997 | Ghaed et al. | |
| 5,705,402 A | 1/1998 | Leland et al. | |
| 5,716,842 A | 2/1998 | Baier et al. | |
| 5,720,922 A | 2/1998 | Ghaed et al. | |
| 5,744,367 A | 4/1998 | Talley et al. | |
| 5,746,974 A | 5/1998 | Massey et al. | |
| 5,779,976 A | 7/1998 | Leland et al. | |
| 5,786,141 A | 7/1998 | Bard et al. | |
| 5,833,925 A | 11/1998 | Shu et al. | |
| 5,965,452 A * | 10/1999 | Kovacs | 436/149 |
| 5,973,443 A * | 10/1999 | Chang et al. | 313/141 |
| 5,993,740 A | 11/1999 | Niiyama et al. | |
| 6,036,840 A * | 3/2000 | Christensen | 205/746 |
| 6,066,448 A | 5/2000 | Wohlstadter et al. | |
| 6,136,268 A | 10/2000 | Ala-Kleme et al. | |
| 6,200,531 B1 | 3/2001 | Liljestrand et al. | |
| 6,207,369 B1 | 3/2001 | Wohlstadter et al. | |
| 6,517,777 B2 | 2/2003 | Liljestrand et al. | |
| 2007/0034529 A1 | 2/2007 | Bard et al. | |

FOREIGN PATENT DOCUMENTS

| | | |
|---|---|---|
| EP | 0 500 305 B1 | 8/1992 |
| EP | 0 791 821 A1 | 8/1997 |
| JP | 1-247962 A | 10/1989 |
| WO | WO 83/01687 A1 | 5/1983 |
| WO | WO 86/02734 A1 | 5/1986 |
| WO | WO 87/07386 A1 | 12/1987 |
| WO | WO 92/14139 A1 | 8/1992 |
| WO | WO 98/12539 A1 | 3/1998 |
| WO | WO 99/14597 A1 | 3/1999 |
| WO | WO 00/03233 A1 | 1/2000 |

OTHER PUBLICATIONS

PCT International Preliminary Examination Report, May 12, 2004.
Supplementary European Search Report concerning Application No. EP 03 76 1242, date of completion of the search, Sep. 26, 2008 (6 pgs.).

* cited by examiner

ELECTROCHEMILUMINESCENCE FLOW CELL AND FLOW CELL COMPONENTS

RELATED APPLICATION

This patent application claims benefit from U.S. Provisional Patent Application No. 60/390,816, entitled: "Electrochemiluminescence Flow Cell and Flow Cell Components", filed Jun. 20, 2002.

FIELD OF THE INVENTION

The present invention relates generally to the field of electrochemiluminescence (ECL), to ECL-based devices and, more particularly, to ECL electrodes. The invention also relates to systems, apparatus, assay cells and flow cells that incorporate ECL electrodes and to methods for conducting ECL-based measurements and assays. The invention also relates to electrochemical assay systems that incorporate an apparatus, assay cell, flow cell or electrode of the present invention, as well as to assay methods utilizing same.

BACKGROUND OF THE INVENTION

Many ECL-based instruments for conducting biological assays and medical tests utilize a reusable flow cell. For an example of such a system, see U.S. Pat. No. 6,200,531. The performance of such flow cells are affected by many factors including, for example, background signal noise, signal drift, electrode etching and carryover. The presence of background signal noise reduces the measurement sensitivity of an ECL-based flow cell. The development of ECL measurement signal drift over time decreases the reproducibility of assay measurements. The deterioration of ECL electrodes due to etching reduces the efficiency of ECL generation. "Carryover," the accumulation of residuals in the flow cell from prior measurements, reduces the reliability of ECL measurements.

An improved flow cell and flow cell components are needed to provide improved performance and increased operational lifetime for ECL-based apparatus.

SUMMARY OF THE INVENTION

An assay apparatus, assay cell or flow cell for conducting electrochemical or ECL assays includes at least one electrode. In an ECL device, the electrode is capable of participating in the generation of ECL. Preferably, an ECL device comprises working and counter electrodes capable of inducing ECL from Ru(bpy)$_3$ in the presence of tripropylamine (TPA). The working and/or counter electrodes may be made of materials other than pure platinum or pure gold; preferably one or more of the electrodes are made of a platinum alloy, rhodium, a rhodium alloy, iridium, or an iridium alloy. Electrodes made of such materials have demonstrated improved properties as compared to conventional Pt electrodes. An electrode may incorporate a field extending element to provide additional pathways for current to flow for improved ECL generation and application of electrical energy. Also, the electrodes may be operated so that the electrode closest to the light detector is maintained at a constant potential or at a potential that is constant relative to a voltage of the photodetector. Advantageously, the disclosed improvements increase apparatus operational lifetime and improve performance in both ECL and electrochemical applications. The invention also relates to assay systems that incorporate the apparatus, assay cell or flow cell of the present invention and to assay methods that utilize the apparatus, assay cell or flow cell of the present invention.

It is an object of the present invention to provide assay apparatus and methodologies for overcoming the deficiencies of the prior art.

It is an object of the present invention to provide apparatus for ECL or electrochemical assays which are more robust with increased operational lifetime and improved performance as compared to the prior art.

It is another object of the present invention to provide improved materials for electrodes for ECL apparatus.

It is a further object of the present invention to provide electrode configurations for improving the application of electrical energy to an assay sample.

It is a further object of the present invention to provide electrode configurations for conducting current in patterns that improve ECL generation.

It is still a further object of the present invention to provide methodologies for conducting assays using electrode materials and electrode configurations of the present invention.

It is still further an object of the present invention to provide apparatus and methodologies for operation of an ECL apparatus to improve ECL detection sensitivity and ECL measurement accuracy.

One aspect of the invention relates to an assay cell, preferably an ECL cell, most preferably an ECL flow cell, comprising a first electrode comprising an alloy capable of inducing electrochemiluminescence, preferably a platinum alloy having a predetermined weight percent of platinum and a predetermined weight percent of a different alloy component (preferably, a transition element, more preferably, Ni, Pd, Co, Fe, Ru, Os, Cr, Mo, Zr, Nb, Ir, Rh, or W, even more preferably Rh or Ir, most preferably Rh or Ir at a weight percentage between 1-80%). Preferably, the ECL cell also comprises a second electrode, an optical detection window and/or, optionally, a reference electrode. More preferably, the assay cell further comprises a cell chamber that comprises a first surface that supports the first electrode (the first electrode preferably being configured to act as a working electrode in an ECL measurement) and an opposing second surface that supports the second electrode (the second electrode preferably being configured to act as a counter electrode) and that has a transparent zone that, preferably, forms at least part of the optical detection window. The invention also relates to an apparatus, preferably an ECL apparatus, comprising said assay cell and, optionally, a light detector.

Another aspect of the invention relates to an ECL apparatus comprising a first electrode (preferably configured to act as a working electrode in an ECL measurement) comprising an alloy capable of inducing electrochemiluminescence, preferably a platinum alloy having a predetermined weight percent of platinum and a predetermined weight percent of a different alloy component (preferably, a transition element, more preferably, Ni, Pd, Co, Fe, Ru, Os, Cr, Mo, Zr, Nb, Ir, Rh, or W, even more preferably Rh or Ir, most preferably Rh or Ir at a weight percentage between 1-80%). Preferably, the apparatus also comprises a second electrode (preferably configured to act as a counter electrode) and, optionally, a reference electrode. More preferably, the assay cell further comprises (e.g., in a cell chamber) a first surface that supports the first electrode and an opposing second surface that supports the second electrode and that has a transparent zone. The invention also may comprise a light detector that is, preferably, in optical registration with said first electrode and said transparent zone.

Another aspect of the invention relates to an assay cell, preferably an ECL cell, most preferably an ECL flow cell, comprising a first electrode that is capable of inducing electrochemiluminescence and comprising a metal electrode material other than pure Pt and Au and, preferably, comprising rhodium, a rhodium alloy, iridium or an iridium alloy. The first electrode, preferably, having a predetermined weight percent of rhodium or iridium and, optionally, a predetermined weight percent of a different alloy component (preferably, a transition element, more preferably, Ni, Pd, Co, Fe, Ru, Os, Cr, Mo, Zr, Nb, Ir, Pt, or W, most preferably Pt). Preferably, the ECL cell also comprises a second electrode, an optical detection window and/or, optionally, a reference electrode. More preferably, the assay cell further comprises a cell chamber that comprises a first surface that supports the first electrode (the first electrode preferably being configured to act as a working electrode in an ECL measurement) and an opposing second surface that supports the second electrode (the second electrode preferably being configured to act as a counter electrode) and that has a transparent zone that, preferably, forms at least part of the optical detection window. The invention also relates to an apparatus, preferably an ECL apparatus, comprising said assay cell and, optionally, a light detector.

Another aspect of the invention relates to an ECL apparatus comprising a first electrode (preferably configured to act as a working electrode in an ECL measurement) comprising a metal electrode material other than pure Pt or Au (preferably rhodium or a rhodium alloy), the first electrode being capable of inducing electrochemiluminescence.

Preferably, the first electrode comprises an alloy having a predetermined weight percent of rhodium and, optionally, a predetermined weight percent of a different alloy component (preferably, a transition element, more preferably, Ni, Pd, Co, Fe, Ru, Os, Cr, Mo, Zr, Nb, Ir, Pt, or W, most preferably Pt). Preferably, the apparatus also comprises a second electrode (preferably configured to act as a counter electrode) and, optionally, a reference electrode. More preferably, the assay cell further comprises (e.g., in a cell chamber) a first surface that supports the first electrode and an opposing second surface that supports the second electrode and that has a transparent zone. The invention also may comprise a light detector that is, preferably, in optical registration with said first electrode and said transparent zone.

Another aspect of the invention relates to an assay cell, preferably an ECL cell, most preferably an ECL flow cell, the flow cell comprising a working electrode capable of inducing electrochemiluminescence and a counter electrode comprising a metal other than pure Pt or Au (preferably, iridium or an iridium alloy, most preferably, a Pt—Ir alloy or, alternatively, rhodium or a rhodium alloy, most preferably a Pt—Rh alloy) and, preferably, an optical detection window. The working electrode may comprise the same electrode material as the counter electrode or may be different (e.g., Pt, a Pt alloy, Ir, a Pt—Ir alloy, Rh, a Pt—Rh alloy, etc.).

Another aspect of the invention relates to an ECL apparatus comprising a working electrode capable of inducing electrochemiluminescence, a counter electrode comprising a metal other than pure Pt or Au (preferably, iridium or an iridium alloy, most preferably a Pt—Ir alloy or, alternatively, rhodium or a rhodium alloy, most preferably a Pt—Rh alloy), and a light detector. The working electrode may comprise the same electrode material as the counter electrode or may be different (e.g., Pt, a Pt alloy, Ir, a Pt—Ir alloy, Rh, a Pt—Rh alloy, etc.).

Another aspect of the invention relates to an assay cell, preferably an ECL cell, most preferably an ECL flow cell, comprising a working electrode and a counter electrode having at least one field extending element. The cell, preferably, further comprises a first surface that supports the working electrode and an opposing second surface that supports the counter electrode, the second surface having a transparent zone. Most preferably, the field extending element extends into or across the transparent zone.

Another aspect of the invention relates to an ECL apparatus comprising a working electrode and a counter electrode having at least one field extending element. The apparatus, preferably, also comprises a first surface that supports the working electrode, an opposing second surface that supports the counter electrode and has a transparent zone; and a light detector, wherein the light detector, the working electrode and the counter electrode are in optical registration. Most preferably, the field extending element extends into or across the transparent zone.

Another aspect of the invention relates to an ECL cell, preferably an ECL flow cell, comprising a working electrode, a counter electrode, a first surface that supports the working electrode, and a second surface that supports the counter electrode and that has a transparent zone, wherein the flow cell is adapted to maintain the counter electrode at a constant potential during an ECL measurement. The cell may optionally comprise a reference electrode and/or a light detector.

Another aspect of the invention relates to an ECL apparatus comprising a working electrode, a counter electrode, a first surface that supports the working electrode, a second surface that supports the counter electrode and that has a transparent zone, and a light detector, wherein the working electrode, the transparent zone and the light detector are in optical registration with each other. The ECL apparatus further comprises a source of electrical energy for inducing ECL (such as a voltage source, a current source or, preferably, a potentiostat) that is adapted to maintain said counter electrode at a constant potential (preferably, ground) or to maintain said counter electrode at a potential that does not vary relative to said light detector. The ECL apparatus may also comprise a reference electrode and the source of electrical energy may comprise a potentiostat and, optionally, a voltage subtraction circuit that outputs a voltage representative of the difference in potential between the working and reference electrodes.

DETAILED DESCRIPTION

Figure 1A:
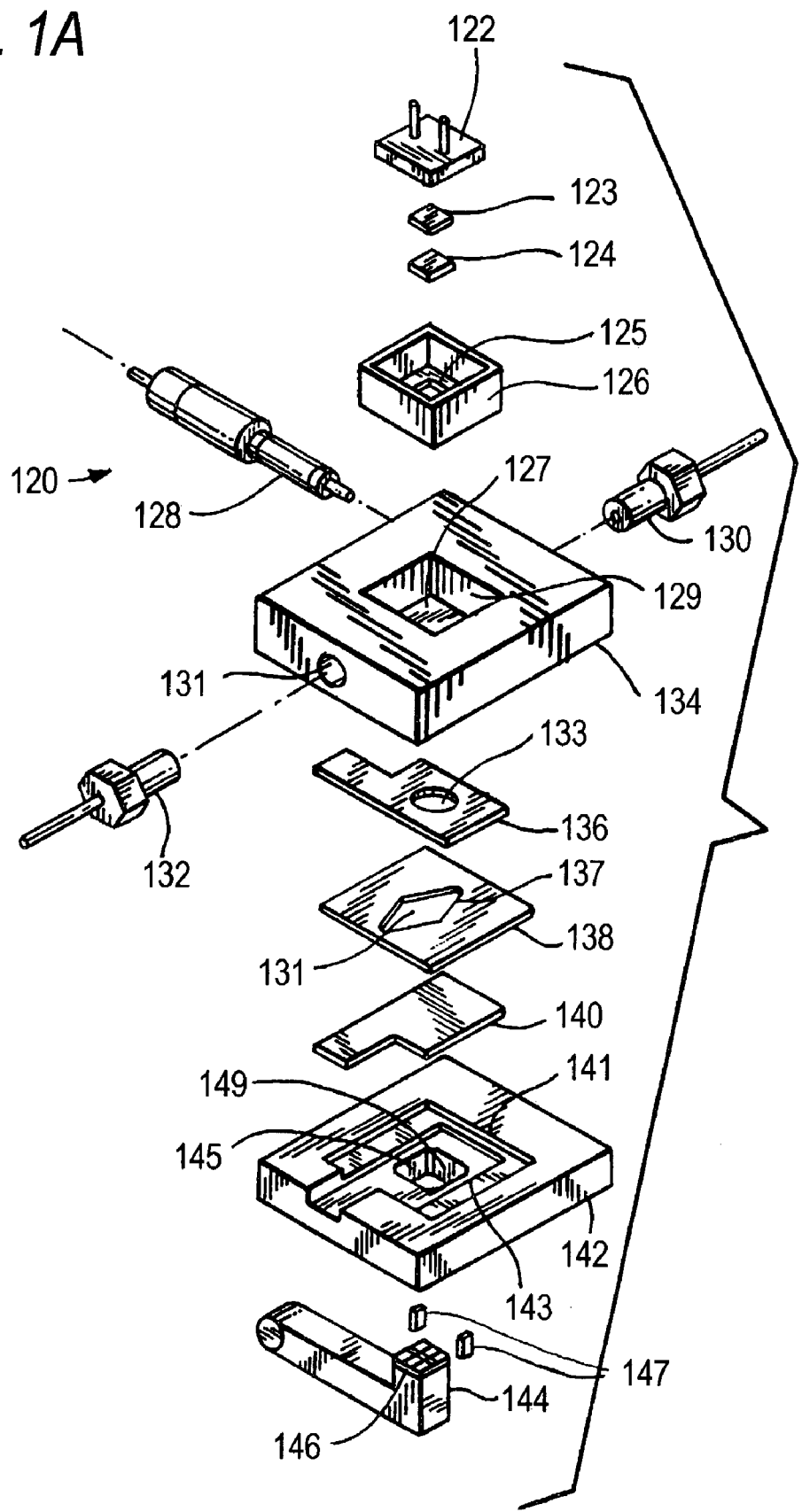
FIGS. 1A and 1B show views of a flow cell for conducting ECL measurements.

All values of electrochemical potentials are relative to the Ag/AgCl reference unless otherwise indicated.

An assay apparatus, assay cell or flow cell for conducting electrochemical or ECL assays according to the present invention includes at least one electrode. The electrode may comprise a material other than pure platinum or pure gold that demonstrates utility in electrochemical or ECL assays. In addition, or alternatively, an electrode may incorporate one or more field extending elements to provide additional pathways for current to flow facilitating the improved application of electrical energy. Also, the electrode may be operated so that it is maintained at a constant potential or at a potential that is constant relative to a voltage of a light detector in or near the apparatus. The disclosed improvements increase apparatus operational lifetime and improve apparatus performance.

The invention includes improved electrodes for conducting ECL measurements that have improved properties (including resistance to etching, low carryover, longer lifetime, lower currents, etc.) than conventional Pt electrodes while, preferably, producing comparable performance in ECL assays. The invention also relates to ECL assay cells (and in particular ECL flow cells) that comprise these improved electrodes.

An ECL assay cell includes at least one electrode, and preferably both a working electrode and a counter electrode, for inducing ECL-active materials to electrochemiluminesce. In addition, the ECL assay cell provides one or more optical paths for allowing the resultant ECL signal to reach a light detector. The optical paths may pass through one or more optical detection windows in the ECL assay cell. Also, ECL assay cells may include: reference electrodes to facilitate control of the working electrode with a potentiostat; a magnet device operable to reversibly collect magnetizable particles (interchangeably referred to throughout as magnetic beads) at the surface of the working electrode; or an integrated light detector and associated optical elements and filters for collecting, processing, and detecting ECL signals.

In an ECL device, an electrode is capable of participating in the generation of ECL. Preferably, an ECL device comprises working and counter electrodes capable of inducing ECL from $Ru(bpy)_3$ in the presence of TPA, at least one of which is not made of pure platinum or pure gold. Preferably one or more of the electrodes are made of a platinum alloy, rhodium, a rhodium alloy, iridium, or an iridium alloy. In addition, or alternatively, an electrode may incorporate a field extending element to provide additional pathways for current to flow to facilitate improved ECL generation and improved application of electrical energy for other ECL device operations. Also, the electrodes may be operated so that the electrode closest to the light detector is maintained at a constant potential or at a potential that is constant relative to a voltage of the light detector.

In certain embodiments, induced ECL is detected by a light detector at a distance, through one or more intervening layers of material. Such intervening layers constitute optical windows through which wavelengths of light of interest may substantially pass. Also, such layers may be electrically conductive to shield the light detector from capacitive noise generated at the electrodes or elsewhere. Field extending elements of the electrode of the present invention may extend in part or entirely across such optical windows.

The invention also relates to assay systems that incorporate the apparatus, an assay cell or a flow cell of the present invention. Such systems preferably further include reagent-handling apparatus, assay reagants, sample-handling apparatus, assay samples and the like. Assay methods utilizing the apparatus, assay cell or flow cell of the present invention demonstrate improved performance.

ECL assay cells configured as flow cells, referred to herein as ECL flow cells, are particularly useful for systems that require reusable ECL assay cells. U.S. Pat. No. 6,200,531 discloses examples of ECL flow cells and ECL apparatus incorporating such flow cells, and the entirety of said patent is hereby incorporated herein by reference (in particular, FIGS. 3A, 3B and 4A-4D, and the accompanying descriptions in the text). It should be noted that while the improved electrodes of the present invention will be described primarily in the context of their implementation in ECL flow cells, such electrodes may be readily implemented in "static" assay cells that do not have a "flow-through" configuration.

Figure 1B:
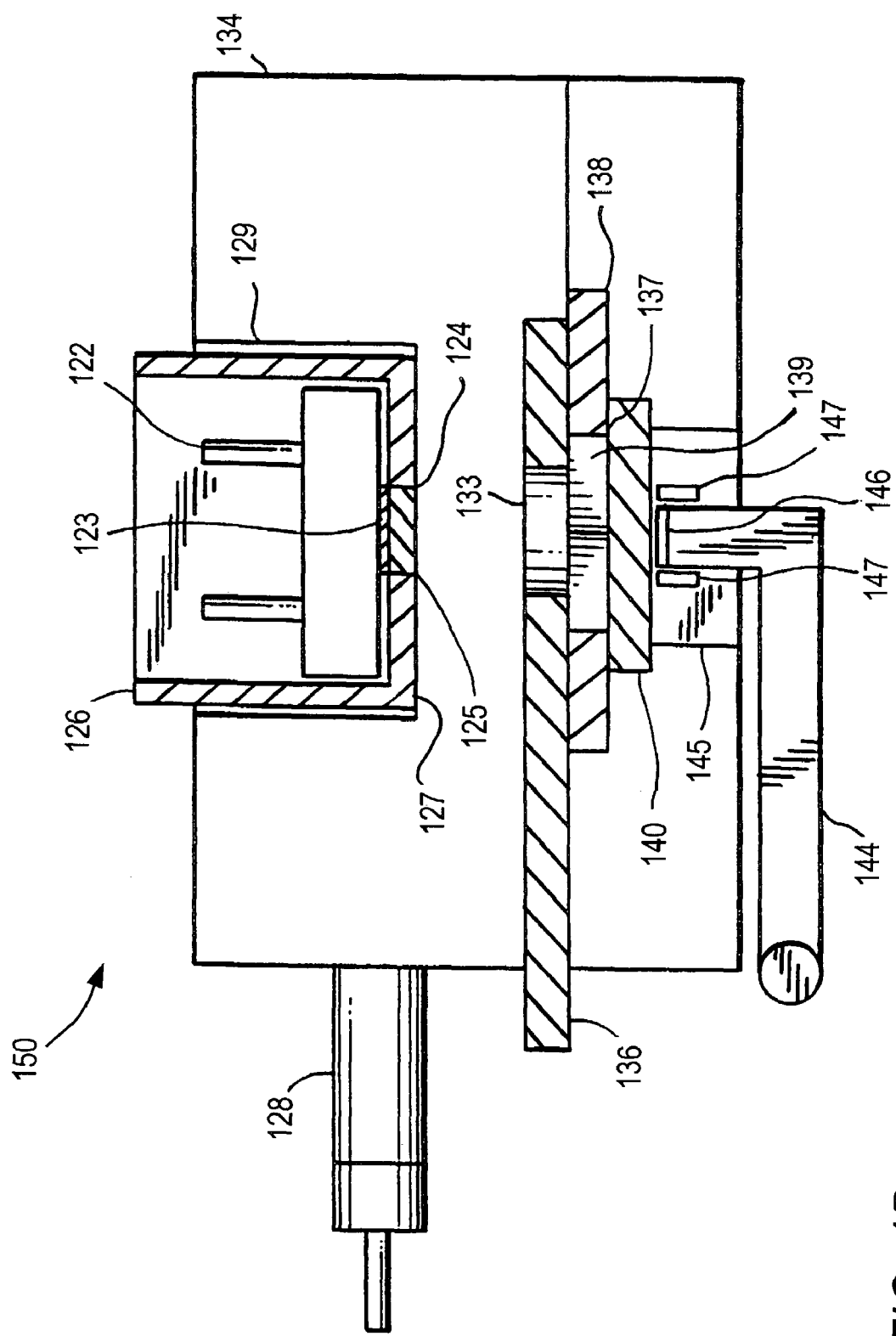

FIGS. 1A and 1B illustrate exploded and cross-sectional views, respectively, of one embodiment of an ECL flow cell 120. Flow cell 120 comprises a light detector 122, an optical filter 123, a conductive window 124, an electrical shield 126 having an opening 125, a reference electrode 128, fluid couplings 130 and 132, a cell component 134 having an optical detection window 127, a counter electrode 136 having an opening 133, a gasket 138 with an opening 137 that defines a portion of flow cell chamber 139, a working electrode 140, and a cell base 142. Optionally, shield 126 and window 124 may be made from one contiguous piece of material. Cell component 134 receives fluid into the flow cell via fluid couplings 130 and 132. Base 142 has an opening 145, to accommodate magnet 146 on pivot arm 144, and a magnet detector 147.

Light detector 122 may be implemented as a photodiode, avalanche photodiode, charge coupled device, CMOS sensor, photomultiplier tube, film, or the like. Alternatively, light detector 122 may comprise an array of light detecting devices, e.g., a photodiode array, a CCD array, a CMOS camera, or the like. Preferably, light detector 122 includes a photodiode.

According to an embodiment of the present invention, an ECL apparatus includes an ECL chamber at least partially defined by the surface of an electrode, preferably the working electrode, and the surface of a substantially transparent structure in the optical pathway between the electrode and the light detector. Preferably, the two surfaces face each other. It is preferred that the structure be a support structure to which a second electrode, preferably the counter electrode, is attached in proximity to the first electrode. In an alternative embodiment, the counter electrode is not directly attached to the support structure and is preferably held in a location between the working electrode and the support structure. The second electrode may partially define a perimeter of the transparent portion of the structure, via one or more openings, apertures, slots, infoldments, or the like. Alternatively, the second electrode is transparent (e.g., a counter electrode made of indium tin oxide, antimony tin oxide, or of a thin metal film that is thin enough (typically <20 nm) to be substantially transparent) so that the second electrode may cover the transparent portion of the structure surface without interfering with its ability to transmit relevant wavelengths of light.

The transparent portion of the structure is in optical registration with at least a portion of the surface of the working electrode so that ECL generated at that surface may be transmitted through the transparent portion to the light detector. For example, referring to FIG. 1B, the portion of component 134 that extends from window 124 to, or through, opening 133 is substantially transparent and chamber 139 is partially defined by a portion of the surface of component 134. Light detector 122 is in optical registration with the portion of working electrode 140 defined by opening 125 and opening 133. Optionally, the light detector may, be integrated into cell 120 or remain external thereto. As a further option, a surface of the light detector itself may define part of the ECL chamber.

A preferred assay apparatus for conducting ECL measurements with an ECL flow cell includes an ECL flow cell, a source of electrical energy for applying electrical energy to the electrodes, a fluidic system for introducing samples and reagents to the flow cell, and electronic or computer controllers for controlling the apparatus, measuring and analyzing ECL signals and providing a user interface. The source of electrical energy is a voltage source, a current source, a potentiostat or the like. The fluidic system may include conventional pumps, valves, probes, reagent bottles and the like.

ECL apparatus of the present invention are preferably adapted to induce and measure ECL from electrochemiluminescent organometallic complexes, more preferably polypyridyl (e.g., bipyridine and phenanthroline-containing) complexes in particular of Ru and Os and, most preferably, from ECL species and labels that comprise Ru(II)(bpy)$_3$ and derivatives thereof. Such derivatives can include substituted bipyridines, especially bipyridines that are substituted with functional groups that are used for linking the label to biomolecules. Preferably, the apparatus operates to induce and measure ECL using any available techniques to induce ECL from polypyridyl complexes of Ru and Os, for example, annihilation and coreactant-based techniques.

Preferably, ECL apparatus according to the present invention measures ECL induced at oxidizing electrodes from the preferred ECL labels in the presence of an ECL coreactant, preferably a molecule that is oxidized to produce a strong reductant, more preferably a tertiary amine, more preferably a trialkylamine, and most preferably tripropylamine (TPA). The coreactant is preferably comprised of an ECL assay buffer which may also include a pH buffering component. Especially preferred ECL assay buffers comprise TPA (preferably, at a concentration greater than or equal to 100 mM), and phosphate as a pH buffering component (preferably, at a concentration greater than or equal to 100 mM and at a pH of 6.5-8.0). Optionally, a surfactant (e.g., a non-ionic surfactant such as Triton X-100, Tween 20 or Thesit), a preservative (e.g., azide, an isothiazolone such as 2-methyl-3(2H)-isothiazolone (MIT) or 5-chloro-2-methyl-3(2H)-isothiazolone (CIT) or an oxazolidine such as BIOBAN CS-1135) or an additional electrolyte (e.g., sodium chloride) may be utilized in the ECL assay buffer.

The mechanism for the generation of ECL from Ru(II)(bpy)$_3$ and related ECL-active species at oxidizing electrodes in the presence of ECL coreactants is believed to involve: (i) oxidation of the ECL-active species to produce an oxidized ECL-active species; (ii) oxidation of the coreactant to produce a strong reductant; (iii) electron transfer from the strong reductant to the oxidized ECL-active species in a highly energetic reaction that regenerates the ECL-active species to its original oxidation state but in an excited electronic state; and (iv) emission of a photon to regenerate the ECL-active species to its original electronic (ground) state. This proposed mechanism is illustrated for Ru(II)(bpy)$_3$ and TPA below:

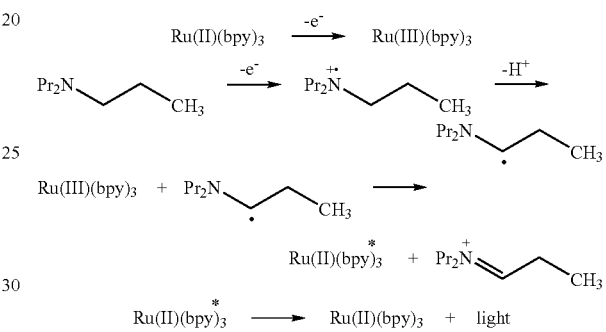

In a preferred operation, a sample comprising an ECL-active species and an ECL coreactant (e.g., in an ECL assay buffer) are introduced into an ECL assay cell, preferably an ECL flow cell. The working electrode is held at a pre-operative potential (POP) during the introduction of the sample (preferred POPs being between −0.8 and 0.8 V vs. Ag/AgCl, more preferably between −0.6 and 0.6 V). An electrochemical potential is then applied to the working electrode (e.g., by applying an electrical potential across the working and counter electrodes in the ECL assay cell, using a potentiostat to achieve a predetermined electrochemical potential at the working electrode relative to a reference electrode) to induce the ECL-active species to electrochemiluminesce. The applied potential oxidizes the ECL-active species and the coreactant at the electrode but avoids substantial oxidation of water (especially preferred ECL excitation potentials range from 1.0-1.8 V, more preferably from 1.1-1.5 V and most preferably 1.2-1.3 V vs. Ag/AgCl). A variety of different electrical waveforms may be used to generate the ECL excitation potential; preferred waveforms are step or ramp waveforms or combinations thereof. The emission of ECL is measured with a light detector.

Subsequent to the generation and measurement of ECL from the sample, the assay cell is preferably cleaned and prepared for measuring a new sample. In one embodiment, a cleaning solution (typically a basic solution comprising a detergent) is introduced and a series of cleaning potentials are applied. It has been found that it is especially advantageous for cleaning to use oxidizing or reducing potentials that are sufficient to generate oxygen or hydrogen gas on the electrode surfaces. Preferred cleaning potentials include oxidizing potentials of at least 1.5 V, more preferably at least 2.0 V, and most preferably approximately 2.0 V; or reducing potentials of at least −1.0 V, more preferably at least −1.5 V, and most preferably approximately −1.5 V. In a particularly preferred cleaning process, the reducing and oxidizing potentials described above are alternated. It may also be desirable to introduce bubbles of air during the cleaning process.

In a preferred cleaning operation, prior to introduction of the sample, the cleaning solution is flushed out of the assay cell by introducing ECL assay buffer. A series of "prepare" potentials are applied to the electrodes during this process. "Prepare" potentials may include alternating step potentials of less magnitude than the cleaning potentials, e.g., oxidizing potentials of more than 0.5 V, more preferably approximately 0.75 V, and reducing potentials of at least −0.3 V, preferably approximately −0.5V.

According to some embodiments of the invention, assays are conducted utilizing magnetizable particles as solid phase supports for ECL assay constituents. Such measurements may involve the measurement of ECL emitted by labels bound to the surface of the particles, e.g., ECL-labeled biomolecules that are bound through biospecific interactions to binding reagents on the surface of the particles. When conducting measurements for assays employing magnetizable particles, a magnetic field is applied near the surface of the working electrode prior to or during the introduction of the sample to collect the magnetizable particles on the surface of the working electrode. For example, with reference to FIG. 1B, pivot arm 144 of cell 120 is pivoted to raise magnet 146 near working electrode 140.

The collected particles are, optionally, washed by flowing ECL assay buffer through the flow cell. ECL is then induced and measured as described above. Preferably, the magnetic field is removed prior to cleaning and preparing the cell for another measurement.

Electrode Materials

During operation of an ECL flow cell incorporating working and counter electrodes made of pure platinum (Pt), both electrodes may deteriorate significantly over time due to etching of the exposed surfaces of the electrodes. Such etching is a major limiting factor upon the operational lifetime of a flow cell. Flow cells have also been observed, in some configurations, to exhibit a downward drift in detected ECL signal and a rise in background signal over the lifetime of the flow cell. Under certain circumstances, the downward drift in signal has been observed to be as much as 10% of the initial signal levels over the course of approximately 2900 measurements. Applicants hypothesize that this downward drift is related to the etching process.

To compensate for such drift, an ECL instrument will need to be recalibrated, have its measurements normalized over the lifetime of the flow cell or have the electrode(s) or flow cell replaced at regular intervals.

Test data indicates that oxidation of the electrode is the primary cause of etching and it is postulated that a significant percentage of the electrode etching observed occurs during the processes of cleaning and regenerating the electrodes between measurements. In particular, in instruments for conducting magnetic bead-based assays, high electric potentials are used to clean the beads from the surface of the working electrode. The application of high potentials during a cleaning cycle causes platinum oxides' to form on the surface of the electrodes. These platinum oxides are loosely bound to the surface and are believed to be released into solution and washed away by cleaning reagent during the cleaning cycle.

Moreover, it has been observed that the Pt dissolved by oxidation may subsequently accumulate or otherwise deposit at locations within the flow cell. When the platinum oxides collect at locations in the optical path between the working electrode and the light detector, e.g., on the optical window, a reduction in light collection efficiency results. Applicants hypothesize that such deposition is one of the causes of ECL signal drift.

For certain flow cell based ECL instruments, optimization of the cleaning step after an ECL measurement may be more important than the measurement step itself for ensuring reproducible ECL measurements. In embodiments that employ magnetizable beads, the cleaning cycle preferably should remove all "used" beads from the working electrode to ensure that there is no "carryover" of signal from one assay to the next.

According to one cleaning process, the voltage applied to the working electrode is pulsed between a reducing voltage and an oxidizing voltage. Preferably, the reducing voltage is low enough to reduce water to create hydrogen gas and the oxidizing voltage is high enough to oxidize platinum and oxidize water to create oxygen gas. In a particularly preferred ECL-based flow cell cleaning sequence, the reducing voltage is −1.5 V and the oxidizing voltage is 2 V (vs. Ag/AgCl). It is believed that both the generation of such gases and the oxidation of Pt resulting from such a cleaning cycle assist in removing beads from the working electrode.

In a cleaning cycle, a cleaning reagent (preferably an aqueous solution comprising a detergent and, optionally, a base such as a hydroxide salt—e.g., an alkali metal hydroxide such as sodium hydroxide or potassium hydroxide—and having a basic pH, preferably greater or equal to 10) may be flowed through the flow cell to flush any solid supports, e.g., magnetizable beads, from the surface of the working electrode. To enhance cleaning effectiveness, air may be introduced during the cleaning cycle, e.g., by introducing bubbles.

In one preferred embodiment, one or both of the working and counter electrodes are fabricated of an electrode material that has an increased oxidation resistance and is, therefore, less prone to etching, to increase the effective operational lifetime of the electrode(s), reduce signal drift and reduce carryover. Electrode materials suitable for use as the working electrode in an ECL-based flow cell preferably exhibit electrochemical characteristics similar to platinum. Specifically, preferred materials oxidize TPA and Ru(bpy)$_3$ at potentials that are lower than the potential for the oxidation of water at that electrode (most preferably, this condition being met for solutions having pH values between 6.5 and 8).

According to a method of the present invention, an ECL label (preferably a luminescent organometallic complex of Ru or Os, more preferably, Ru(bpy)$_3$ or a derivative thereof) is induced to electrochemiluminesce in the presence of an ECL coreactant (preferably, a tertiary amine, most preferably, TPA) by applying a potential to a working electrode, wherein: (i) the working electrode and, optionally, the counter electrode is a metal electrode other than pure Pt or Au; (ii) said potential is sufficient to oxidize the ECL label and the ECL coreactant; and (iii) the applied potential produces a current density from the oxidation of the coreactant that is at least equal (more preferably at least two times, even more preferably at least 5 times, even more preferably at least 10 times) the current density from the oxidation of water.

In another embodiment of the present invention, the working and, optionally, the counter electrode, of an ECL flow cell comprises a metal or metal alloy, other than pure platinum or gold, that at an electrochemical potential of 1.3 V vs. Ag/AgCl—approximately the oxidation potential of Ru(II)(bpy)$_3$—exhibits a current density during the oxidation of water of less than 5 mA/cm$^2$; preferably in water comprising electrolytes at a pH of 6.5-8, more preferably in a phosphate-buffered aqueous solution having a pH of 6.5-8.0; and most preferably in a solution comprising 200-400 mM $KH_2PO_4$, 50-200 mM NaCl, surfactant and sufficient KOH to adjust the PH to 6.6-6.8.

In another embodiment of the present invention, the working and, optionally, the counter electrode, of an ECL flow cell comprises a metal or metal alloy, other than pure platinum or gold, that oxidizes TPA more readily than water. Preferably, this condition is met at an electrochemical potential at which $Ru(II)(bpy)_3$ is oxidized, most preferably 1.3 V. In one preferred embodiment, the ratio of the electrochemical currents measured at the electrode at a potential of 1.3 V for 150 mM TPA in phosphate buffer at a pH of 6.5-8.0 (most preferably, 150 mM TPA, 50-200 mM NaCl, 200-400 mM phosphate, and surfactant, at a pH of 6.6-6.8) to the electrochemical current measured in an analogous buffer that does not contain TPA (e.g., the same buffer solution at the same pH with TPA replaced by an appropriate pH adjuster) is at least one, more preferably at least two, more preferably at least 5, and most preferably at least 10.

According to an embodiment of the present invention, certain Pt alloys have been identified as suitable replacements for Pt working electrodes or counter electrodes in ECL flow cells. Surprisingly, it has been discovered that alloys of transition elements with Pt have electrochemical properties very similar to Pt but have advantages over pure Pt when used in ECL devices. These advantages have been found to include improved resistance to electrochemical etching, reduced drift in ECL signal, reduced carryover and longer electrode operational lifetime. Preferably, the Pt alloys comprise Pt combined with a second transition element that is present at a weight percentage of 1-50%, more preferably 5-50%, more preferably 10-30%, and most preferably approximately 10%. Suitable alloys for ECL electrodes are alloys of Pt with Ni, Pd, Co, Fe, Ru, Os, Cr, Mo, Zr, Nb, Ir, Rh, or W; more preferably, alloys of Pt with Ir, Rh or W; and, most preferably, alloys of Pt with Ir.

In one preferred embodiment, an ECL electrode is formed of a Pt—Ir alloy wherein the weight percent of iridium in the alloy is 1-50%, more preferably 5-50%, more preferably 10-50%, even more preferably 10-30%, and even more preferably approximately 10%.

In another preferred embodiment, an ECL electrode is formed of a Pt—Rh alloy wherein the weight percent of rhodium in the alloy is 1-50%, more preferably 5-50%, more preferably 10-50%, even more preferably 10-30%, and even more preferably approximately 20%.

According to another embodiment of the invention, an electrode of an ECL assay cell comprises, consists essentially of or consists of a transition element other than pure Pt or Au, preferably Ni, Pd, Co, Fe, Ru, Os, Cr, Mo, Zr, Nb, Ir, Rh or W; more preferably, Rh or Ir; and most preferably, Ir.

According to another embodiment of the invention, the counter electrode of an ECL assay cell comprises an alloy of Pt and a transition element, the weight percentage of the transition element being, preferably, 1-99%, more preferably 5-50%, more preferably 5-30%, and most preferably 10-30%. The remainder of the alloy may be substantially Pt or it may include an additional component as well. The transition element is preferably Ni, Pd, Co, Fe, Ru, Os, Cr, Mo, Zr, Nb, Ir, Rh or W; more preferably, Rh or Ir; and most preferably, Ir. In an alternate preferred embodiment, the working electrode is Au or, preferably, Pt. In another alternate preferred embodiment, the working electrode is made from a Pt alloy, preferably a Pt—Ir alloy. In another alternate preferred embodiment, the working electrode is a pure transition element other than Pt or Au, e.g., Rh.

According to another embodiment of the invention, the counter electrode of an ECL assay cell is formed of an alloy that comprises, consists essentially of, or consists of Pt and Ir. The weight percentage of Ir is, preferably, 1-99%, more preferably 5-50%, more preferably 5-30%, and most preferably 10-30%. In one preferred embodiment, the working electrode is Au or, preferably, Pt.

In another preferred embodiment, the working electrode is formed of a Pt alloy, preferably a Pt—Ir alloy (most preferably, the same alloy as comprises the counter electrode). In another preferred embodiment, the working electrode is a pure transition element other than Pt or Au, e.g., Rh.

According to another embodiment of the invention, the counter electrode of an ECL assay cell comprises an alloy of Ir and a transition element, the weight percentage of the transition element being, preferably, 1-99%, more preferably 5-50%, more preferably 5-30%, and most preferably 10-30%. The remainder of the alloy may be substantially Ir or it may include an additional component as well. The transition element is preferably Ni, Pd, Co, Fe, Ru, Os, Cr, Mo, Zr, Nb, Rh and W. In an alternate preferred embodiment, the working electrode is Au or, preferably, Pt. In another alternate preferred embodiment, the working electrode is a made from a Pt alloy, preferably a Pt—Ir alloy. In another alternate preferred embodiment, the working electrode is a pure transition element other than Pt or Au, e.g., Rh.

In still further alternative embodiments, the working electrode of an ECL assay cell comprises an alloy of Ir or Rh and a transition element, the weight percentage of the transition element being, preferably, 1-99%, more preferably 5-50%, more preferably 5-30%, and most preferably 10-30%.

According to another embodiment of the invention, the counter electrode of an ECL assay cell comprises an alloy of Rh and a transition element, the weight percentage of the transition element being, preferably, 1-99%, more preferably 5-50%, more preferably 5-30%, and most preferably 10-30%. The remainder of the alloy may be substantially Rh or it may include an additional component as well. The transition element is preferably Ni, Pd, Co, Fe, Ru, Os, Cr, Mo, Zr, Nb, Ir, or W; most preferably, Ir. In an alternate preferred embodiment, the working electrode is Au or, preferably, Pt. In another alternate preferred embodiment, the working electrode is a made from a Pt alloy, preferably a Pt—Ir alloy. In another alternate preferred embodiment, the working electrode is a pure transition element other than Pt or Au, e.g., Rh.

Advantageously, the counter electrode in an ECL cell has over-potentials for the oxidation and/or reduction of water that are less than that of Pt (preferably, by 50 mV or more, more preferably by 100 mV or more, most preferably by 200 mV or more). Such reductions in over-potential will be directly translated into lower cell potentials during cell cleaning.

The working and counter electrodes are preferably generally planar and may take a variety of different forms including thin films, sheets, foils, wires, screens, meshes, or the like. Thin films may be made by conventional methods including those used in the manufacture of circuit boards and microelectronics, e.g., by deposition of the film on a substrate via evaporation, chemical vapor deposition, sputtering, screen printing, electrodeposition, electroless deposition and the like. The electrodes may be patterned, configured or given a specific shape or geometry via patterned deposition, molding, lithography, machining, electroforming, laser ablation, patterned etching (e.g., reactive ion etching), and the like. The electrodes of the invention may be made of metal or a metal alloy. In alternate embodiments of the invention, they are composite materials that comprise a metal or metal alloy.

Electrode Geometry

According to an embodiment of the invention, the counter electrode is configured with one or more field extending elements (e.g., electrode projections) that extend into or across the optical path of the light detector but leave openings or substantially transparent areas in the counter electrode through which light is transmitted. These field extending elements, by extending into or across the optical path of the light detector decreases the amount of light incident upon the light detector (preferably, by less than 50%, more preferably less than 25%, and most preferably less than 10%) but, advantageously, may establish a substantially even distribution of current across the working electrode (e.g., during an ECL measurement or cleaning cycle) by decreasing the distance that current must travel through solution. Preferably, the maximum distance between a point on the surface of the working electrode that is in optical registration with the light detector and the point on the surface of the counter electrode closest thereto is less than 4 times the distance between the working electrode and the counter electrode, hereinafter the "height of the cell," more preferably less than 2.5 times the height of the cell, even more preferably less than 2.0 times the, height of the cell, and most preferably less than 1.5 times the height of the cell. This ratio is referred to herein as the "current path aspect ratio." For purposes of illustration, the height of cell 150 in FIG. 1B is equal to the thickness of gasket 138.

Working electrode 140 in FIGS. 1A and 1B has (i) a "visible" region that is in optical registration with opening 133 of counter electrode 136 and light detector 122 and (ii) a "hidden" region that is directly opposite counter electrode 136 and not visible to, light detector 122. In magnetic bead based assays, the collection of magnetizable particles is advantageously confined to the "visible" region in order to maximize collection of ECL from the particles. During operations such as ECL measurement and electrode cleaning that may require high current densities, the current to the "visible" region of the working electrode is less than the current to the "hidden" region. The difference in current densities is due to the longer distance between the counter electrode and the "visible" region relative to the "hidden" region and the corresponding differences in the voltage drop through the solution between the counter and working electrodes. Therefore, during operations such as ECL measurement and electrode cleaning, a cell potential that generates a current at the "visible" region that is appropriate for generating ECL or cleaning the electrode may generate at the "hidden" region much higher currents that can accelerate etching and degradation of the electrode. Advantageously, counter electrode 136 may be modified with field extending elements so as to establish more even distributions of current across the working electrode.

Preferably, the counter electrode defines the perimeter of a window in the optical path between the working electrode and the light detector or, alternatively, a closed curve may be defined within the counter electrode material that completely surrounds the window region. Alternatively, the window region is not completely surrounded by the counter electrode. In another alternate embodiment, the window region is defined by the region between two or more counter electrodes.

In one preferred embodiment, the field extending elements are projections that form an interdigitated array. In another preferred embodiment, at least some field extending elements extend completely across the optical path, preferably, to form one or more openings whose perimeter is completely defined by the counter electrode. The field extending elements may extend the electrical field generated at the counter electrode into the optical path so as to generate a more even distribution of electrical current over the entire working electrode. The potentials and currents required to induce ECL or clean the working electrode in an assay cell comprising a counter electrode with a field extending element may be substantially reduced as compared to prior assay cells, thus reducing the etching of the electrodes, reducing ECL signal drift and extending the lifetime of the cell. Preferably, the oxidizing potential applied to the working electrode of an ECL flow cell having a counter electrode with field extending elements according to the present invention during a cleaning cycle is no greater than 1.75 V and, more preferably, no greater than 1.5 V.

Figure 2A:
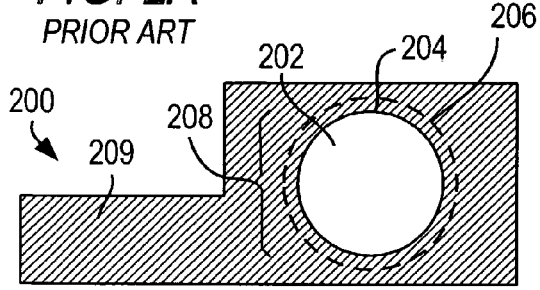
FIGS. 2A-2J illustrate embodiments of counter electrodes according to embodiments of the invention.

FIG. 2A shows counter electrode 200 that is analogous to counter electrode 136 of cell 120 (as shown in FIGS. 1A and 1B). Counter electrode 200 defines an opening 202, having a perimeter 204 that is completely defined by counter electrode 200, e.g., a closed curve 206 (represented by a dashed line) may be defined in counter electrode 200 that completely surrounds opening 204. Counter electrode 200 has an ECL-active region 208, for registration with a working electrode (not shown), and an electrical contact element 209 that conducts electrical energy to ECL-active region 208 and provides a location for electrical contact. Optionally, contact element 209 may be omitted or substantially altered in shape to provide alternate locations for electrical contact. Importantly, counter electrode 200 does not include a field extending element that extends across the optical path between the working electrode and the light detector.

According to embodiments of the present invention, counter electrode 136 in cell 120 can be replaced with a counter electrode having a configuration with field extending elements as illustrated in FIGS. 2B-2J. In alternate embodiments, electrodes with field extending elements of the present invention are advantageously implemented in assay cells, electrochemical assay cells, ECL assay cells, electrochemical apparatus and ECL apparatus.

Figure 2B:
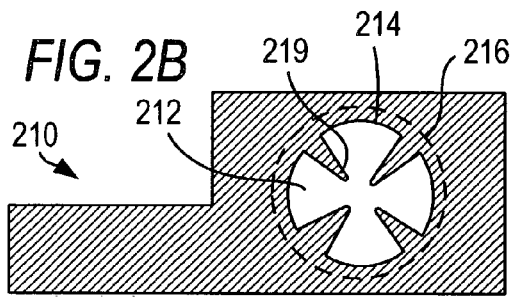

FIG. 2B shows counter electrode 210 that defines a window region 212 having a perimeter 214 that is completely defined by counter electrode 210. A closed curve 216 (represented by a dashed line) may be defined in counter electrode 210 that completely surrounds window region 212. Counter electrode 210 also comprises field extending elements 219 that extend into window region 212 and, thus, preferably, into the optical path between the working electrode and the light detector.

Figure 2C:
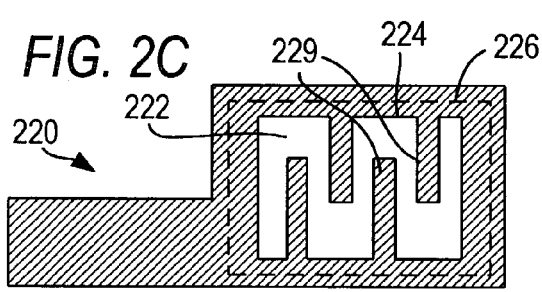

FIG. 2C shows counter electrode 220 that defines a window region 222 having a perimeter 224 that is completely defined by counter electrode 220. A closed curve 226 (represented by a dashed line) may be defined in counter electrode 220 that completely surrounds window region 222. Counter electrode 220 also comprises field extending elements 229 configured as an interdigitated array that extend into window region 222 and, thus, preferably, into the optical path between the working electrode and the light detector.

Figure 2D:
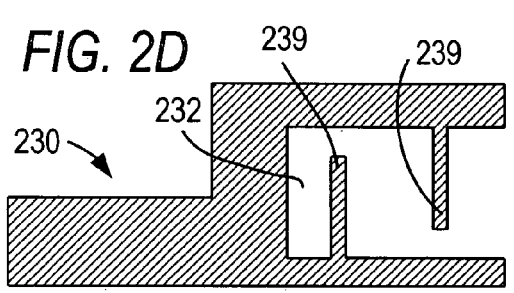

FIG. 2D shows counter electrode 230 that includes a window region 232 having a perimeter that is partially defined by counter electrode 230. Counter electrode 230 also comprises field extending elements 239 that extend into window region 232 and, thus, preferably, into the optical path between the working electrode and the light detector.

Figure 2E:
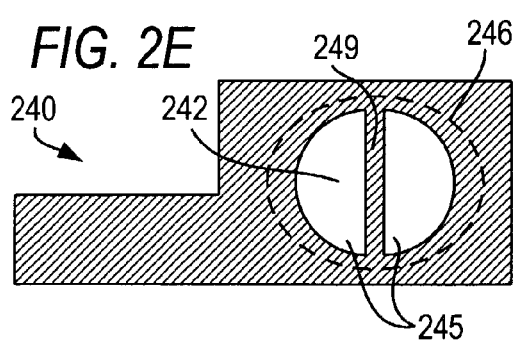

FIG. 2E shows counter electrode 240 that includes window region 242 with a field extending element 249 that extends across window region 242 to form openings 245 that have perimeters that are completely defined by counter electrode 240. A closed curve 246 (represented by a dashed line) may be defined in counter electrode 240 that completely surrounds window region 242. It is preferred that field extending element 249 extends across the optical path between the working electrode and the light detector.

Figure 2F:
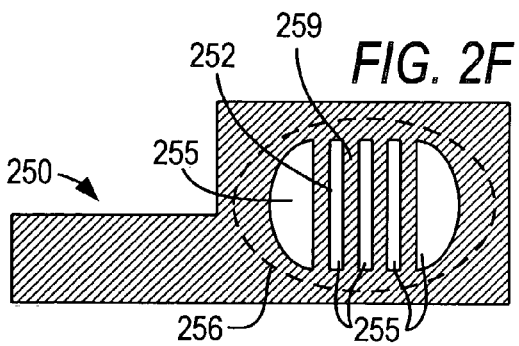

FIG. 2F shows counter electrode 250 that includes window region 252 with field extending elements 259 that extend across window region 252 to form openings 255 that have perimeters that are completely defined by counter electrode 250. A closed curve 256 (represented by a dashed line) may be defined in counter electrode 250 that completely surrounds window region 252. It is preferred that field extending elements 259 extend across the optical path between the working electrode and the light detector. Electrodes, such as counter electrode 250, having one or more non-intersecting field extending elements that extend across a window region are referred to herein as "ladder" electrodes.

Figure 2G:
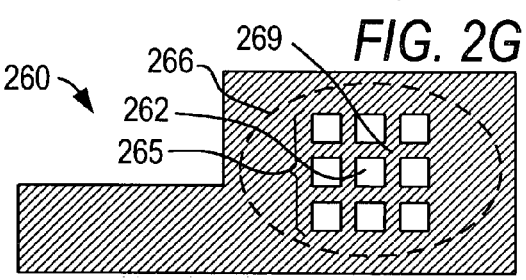

FIG. 2G shows counter electrode 260 that includes window region 262 with field extending elements 269 in the form of a grid that extend across window region 262 to form openings 265 that have perimeters that are completely defined by counter electrode 260. A closed curve 266 (represented by a dashed line) may be defined in counter electrode 260 that completely surrounds window region 262. It is preferred that field extending elements 269 extend across the optical path between the working electrode and the light detector.

Figure 2H:
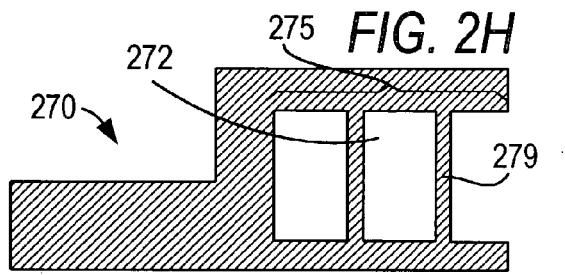

FIG. 2H shows counter electrode 270, that includes a window region 272, having field extending elements 279 that extend across window region 272 to form openings 275 that have perimeters that are completely or partially defined by counter electrode 270. It is preferred that field extending elements 279 extend across the optical path between the working electrode and the light detector.

Figure 2I:
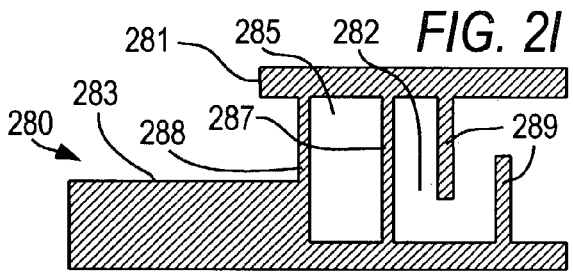

FIG. 2I shows counter electrode 280 comprising conducting elements 281 and 283. Counter electrode 280 defines a window region 282 between conducting elements 281 and 283 with field extending elements 287 and 288 that extend between conducting elements 281 and 283 to form multiple openings 285 that have perimeters that are completely or partially defined by counter electrode 280. Counter electrode 280 also comprises field extending elements 289 that extend into window region 282. Optionally, any of elements 287, 288 and 289 may be omitted. It is preferred that one or more of field extending elements 287, 288 and 289 extend into or across the optical path between the working electrode and the light detector.

Figure 2J:
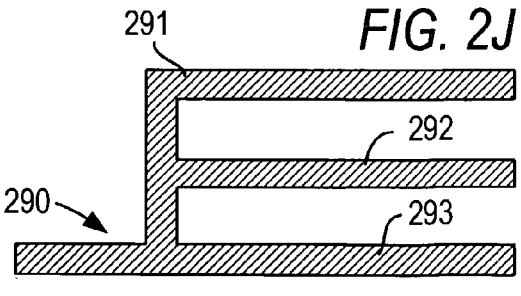

FIG. 2J shows counter electrode 290 comprising conducting elements 291, 292 and 293. It is preferred that field extending elements 291, 292 and 293 extend into or across the optical path between the working electrode and the light detector. Optionally, field extending elements 291 and 293 may be omitted.

In alternate embodiments, field extending elements may be configured in a variety of other shapes, e.g., with straight or curved edges. Also, the field extending elements in a flow cell may be oriented in different directions relative to the flow of fluid in the flow cell (e.g., diagonal, parallel, perpendicular, or the like).

Preferably, one or more field extending elements, more preferably all of the field extending elements, are substantially linear in shape and are oriented substantially parallel to the flow of fluid in a flow cell. In such configurations, electrode material that is etched from the surface of a field extending element will tend to flow parallel to the orientation of the field extending element and, advantageously, redeposit on the element itself and not on other surfaces in the flow cell.

Another advantage of the counter electrode configurations of the present invention is that in an ECL cell, the field extending elements of the counter electrode may significantly reduce the distance between points on the surface of the working electrode, most preferably, points in optical registration with the light detector during an ECL measurement, and points on the counter electrode. For example, the optical path may extend from the working electrode through openings in the counter electrode, the transparent portion of the opposing cell wall, and any additional optical elements (mirrors; lenses, filters, prisms, etc.) to the light detector.

According to an embodiment of the present invention, an ECL apparatus includes an ECL chamber at least partially defined by the surface of an electrode, preferably a working electrode, e.g., working electrode 140 of flow cell 120, the surface of a substantially transparent structure in the optical pathway between the electrode and the light detector (e.g., optical detection window 127 of flow cell 120), and the field extending elements of a counter electrode. Preferably, the surface of the first electrode faces the other two surfaces. It is preferred that the structure be a support structure to which a second electrode, preferably, the counter electrode, is attached in proximity to the first electrode (e.g., counter electrode 136 of cell 120 having opening 133). The second electrode may partially define a perimeter of the transparent portion of the structure, via one or more openings, apertures, slots, infoldments, or the like. The field extending elements extend into or across the optical pathway. The transparent portion of the structure is in optical registration with at least a portion of the surface of the first electrode so that ECL generated at that surface may be transmitted through the transparent portion to an integrated or external light detector (e.g., light detector 122 of cell 120).

Preferably the field extending elements are configured so as to block or otherwise interfere with less than 50%, more preferably less than 25% and most preferably less than 10% of the light generated at the surface of the first electrode or that would otherwise be incident upon the light detector.

Preferably, the maximum distance between a point on the surface of the working electrode in optical registration with the light detector and a point on the surface of the counter electrode in the optical path (or, if none, closest to the optical path) is less than 4 times the height of the cell (e.g., the distance between the planes defined by the working electrode and the counter electrode), more preferably less than 2.5 times the height of the cell, even more preferably less than 2.0 times the height of the cell and most preferably less than 1.5 times the height of the cell.

Application of Electrical Potentials to Electrodes

The generation of ECL in an ECL cell generally involves the application of an electrical potential across at least two electrodes. In a preferred embodiment of the invention, an ECL instrument is configured so that the closest of the electrodes to the light detector (preferably a counter electrode) is held, during the induction and measurement of ECL, at a constant potential, most preferably at the ground potential. In another preferred embodiment, an ECL instrument is configured so that the closest of the electrodes to the light detector (preferably a counter electrode) is held at the same potential as a voltage of the light detector (preferably a photodiode), most preferably at ground. In another preferred embodiment, an ECL instrument is configured so that the closest of the electrodes to the light detector (preferably a counter electrode) is at a potential that does not vary relative to a voltage of the light detector (preferably a photodiode). Alternatively, the closest of the electrodes to the light detector is at the same voltage or at a voltage that does not vary relative to the case or electrical shielding surrounding the light detector.

Preferably, a potentiostat is used to control the potential at the working electrode. When the working electrode is grounded, the ECL cell may be controlled using a three electrode system and a conventional potentiostat circuit. The potentiostat measures the voltage difference between a reference electrode and the grounded working electrode (i.e., the voltage at the reference electrode relative to ground). The potentiostat adjusts the voltage at the counter electrode to achieve a desired voltage at the reference electrode (and by extension, a desired voltage difference between the working electrode and the reference electrode).

This potentiostat circuit may be adapted to control a three electrode system having a grounded counter electrode by the addition of a voltage subtraction circuit. The voltage subtraction circuit takes as inputs the voltages at the working and reference electrodes and outputs a voltage that is representative of the difference in the potentials at these two electrodes. The potentiostat is connected to the output of the voltage subtraction circuit, the counter electrode and the working electrode and adjusts the potential at the working electrode until the output of the voltage subtraction circuit reaches a desired value.

Advantageously, maintaining the electrode closest to the light detector at constant potential (or at a potential that does not vary relative to a voltage of the light detector) reduces the noise component of the signal produced by the light detector during an ECL measurement that results from capacitive coupling of the electrodes to the light detector. The capacitive coupling is minimized by maximizing the distance between the light detector and the electrode that varies in potential. Also, the capacitive coupling is further minimized because the grounded electrode acts to shield the light detector from the other electrode. Preferably, no additional shielding device is required in the optical path between the working electrode and the light detector.

According to an embodiment of the present invention, an ECL apparatus includes an ECL chamber at least partially defined by the surface of an electrode, preferably the working electrode, e.g., working electrode 140 of flow cell 120, of a substantially transparent structure in the optical pathway between the electrode and the light detector (e.g., optical detection window 127 of flow cell 120). Preferably, the two surfaces face each other. It is preferred that the structure be a support structure to which a second electrode, preferably the counter electrode, is attached in proximity to the first electrode. The second electrode may partially define a perimeter of the transparent portion of the structure, via one or more openings, apertures, slots, infoldments, or the like (e.g., counter electrode 136 of cell 120 having opening 133). The transparent portion of the structure is in optical registration with at least a portion of the surface of the first electrode so that ECL generated at that surface may be transmitted through the transparent portion to an integrated or external light detector (e.g., light detector 122 of cell 120).

Figure 16:
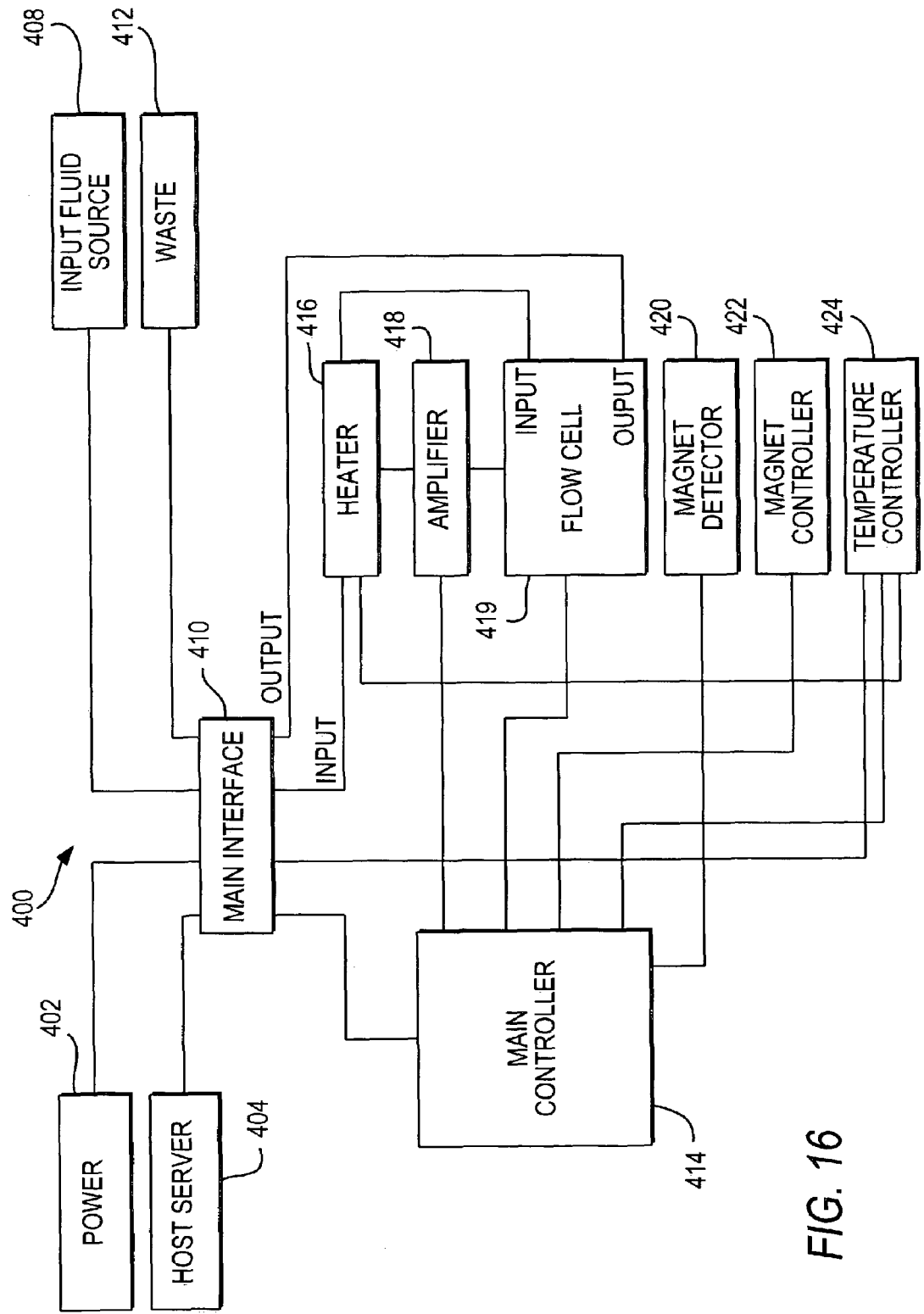
FIG. 16 is a diagram of an ECL apparatus according to an embodiment of the invention.

FIG. 16 illustrates an assay apparatus 400 according to an alternate embodiment of the present invention. Apparatus 400, which alone may comprise an ECL system or form a component of a larger ECL system, is analogous in structure and function to the apparatus shown in FIG. 5 of U.S. Pat. No. 6,200,531. Apparatus 400 comprises a power supply 402, a host interface 404, input fluid source 408, main interface 410, waste output 412, main controller 414, heater 416, amplifier 418, flow cell 419, magnet detector 420, magnet controller 422, and temperature controller 424. Preferably, a potentiostat according to the present invention is included in main controller 414.

In operation, the apparatus is adapted to keep the counter electrode at a constant potential, preferably ground, or, alternatively, maintain it at a potential that does not vary relative to a voltage of the light detector. Preferably, the apparatus further comprises a reference electrode and the potential at the working electrode is controlled using a potentiostat connected to the counter electrode, the working electrode and the reference electrode. Most preferably, the apparatus controls the potential difference between the working electrode and the reference electrode by adjusting the voltage applied to the working electrode.

EXAMPLES

Buffer Compositions: "TPA Assay Buffer" refers to a TPA containing buffer consisting of 0.15 M TPA in a buffer of potassium phosphate, salt and surfactant at a pH of approximately 6.8 (ORI-GLOW® Plus, IGEN International) that provides an appropriate environment for the generation of ECL from $Ru(II)(bpy)_3$ and derivatives. "Cleaning Solution" refers to a solution (0.1 M KOH, 0.15 M NaCl and 0.4% Triton) used to clean the working electrode in an ECL instrument and to remove magnetizable or paramagnetic beads (magnetizable beads and paramagnetic beads are interchangeably referred to throughout) from the surface of the working electrode.

Calibration Reagents: ORIGEN® M-Series® positive calibrator (PC) was used as a positive control and TPA Assay Buffer was used as a negative control (NC) for the ECL experiments described below. The positive calibrator consisted of 2.8 µm Dynal superparamagnetic beads that are coated with a layer of protein labeled with ORI-TAG® NHS Ester (IGEN International, Inc.), a derivative of ruthenium (II)-tris-bipyridine. The bead concentration is 33 µg/ml (approximately 500,000 beads in a 200 µl sample).

Electrode materials: Pt electrodes were obtained from D. F. Goldsmith Chemical and Metal Corporation (Evanston, Ill.). The electrodes are 0.005" thick and are 99.99% Pt. Pt-10% Ir electrodes were obtained from Goodfellow Corporation (Berwyn, Pa.). The designation Pt-X % M is used herein to refer to a platinum alloy that includes X % of metal M. A typical material composition was 50 ppm Cu, 75 ppm Au, 10% Ir, 250 ppm Fe, <100 ppm Ni, <50 ppm Si, 100 ppm Ag, balance Pt. The Ir electrodes are 0.005" thick foils from Alfa Aesar (Pittsburgh, Pa.).

Example I

ECL Measurements

ECL measurements were conducted using a flow cell from an ORIGEN® M8 Analyzer (IGEN International, Inc.). The flow cell was configured analogously to the flow cell pictured in FIGS. 1A and 1B. The working and/or counter electrodes were either platinum or replaced with alternate materials as described below. The electrochemical potential between the working electrode and an Ag/AgCl reference electrode was controlled using a potentiostat. All values of electrochemical potentials are relative to the Ag/AgCl reference unless otherwise indicated.

Figure 3:
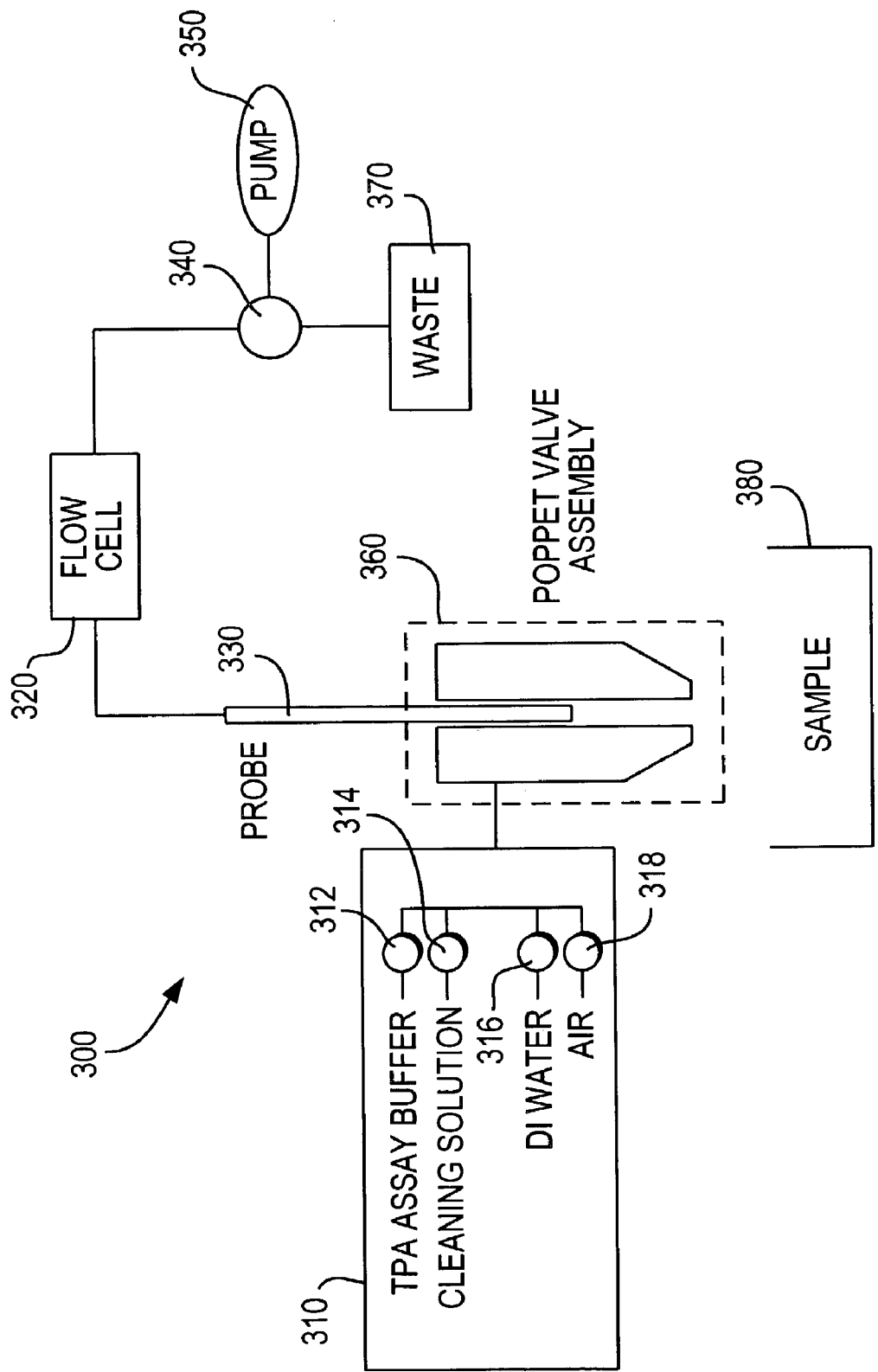
FIG. 3 is a diagram of a system for conducting ECL measurements.

The system fluidic diagram is shown in FIG. 3. System 300 comprises inlet manifold 310, flow cell 320, probe 330, valve 340, pump 350, poppet valve assembly 360, waste receptacle 370, and sample container 380. Inlet manifold 310 comprises valve 312 connected to a source of TPA Assay Buffer, valve 314 connected to a source of Cleaning Solution, valve 316 connected to a source of deionized water, and valve 318 connected to a source of air.

Fluid was aspirated through probe 330 into flow cell 320 by a positive displacement pump 350. Samples were drawn from wells of multi-well plates 380 by lowering probe 330 through poppet valve assembly 360 (analogous to the one pictured in FIG. 11 of U.S. Pat. No. 5,720,922) or, alternately, reagents or air were drawn from inlet manifold 310 by raising probe 330 into poppet valve assembly 360. Air or the appropriate reagents were selected through the use of valves 312, 314, and 316 in the inlet manifold 310. The application of potentials, the motion of plates, the flow of sample and reagents through flow cell 320 and the collection of data was all under computer control.

In a typical measurement cycle, a sample in a 96-well or 384-well plate 380 was mixed to resuspend any magnetic beads in the samples. The sample was then drawn into flow cell 320 and the beads were captured on the working electrode using a sandwich magnet located on the opposite side of the electrode (the working electrode was held at a pre-operative potential (POP) during this process; a POP of 0 V was used for these experiments). The beads were washed by passing TPA Assay Buffer through flow cell 320 so as to reduce non-specific binding to the electrode. Next, the excitation potential (1.26 V) was applied and the emitted ECL was measured by a photodiode (see FIG. 1A) using a transimpedance amplifier circuit.

Cleaning Solution and intermittent air bubbles were then introduced into flow cell 320 while cleaning potentials were applied (with the magnet moved away from the electrode) to remove beads from and clean the working electrode (the cleaning potentials comprised a series of step potential pulses alternating between −1.5 V and 2 V). Finally, TPA Assay Buffer was passed through flow cell 320 to remove the Cleaning Solution and a "prepare" potential was applied to the working electrode (comprising a series of step potential pulses alternating between 0.75 V and −0.5 V) to prepare flow cell 320 for the next measurement. Prior to the introduction of the next sample, the working electrode potential was adjusted to the pre-operative potential.

It is important to note that the experiments described in Examples II and III below were designed to evaluate the relative performance of different electrode materials. The absolute values of some of the parameters that were measured (e.g., signal drift and carryover) are dependent on the exact experimental conditions and are not necessarily fully optimized.

Example II

Comparison of ECL Measurements Using Ir, Pt and Pt—Ir Electrodes

A. Methods: ECL was measured in flow cells having Pt, Ir or Pt-10% Ir electrodes (working and counter) in the presence of positive calibrator (as a positive control to measure the effect of the electrode on ECL signal) or TPA Assay Buffer (as a negative control to measure the effect of the electrode on background signal in the absence of ORI-TAG). Samples (250 μL) were pipetted into the wells of a 96-well plate. The samples (200 μL) were aspirated into the flow cell after resuspension of the beads. There was little difference in the optimal excitation potential for the three materials; a typical value that was used was 1260 mV vs. Ag/AgCl (oxidation).

Drift was determined over a 100-plate study (about 10,000 samples) for flow cells with Pt or Pt-10% Ir electrodes. Tests were run in batches of eight plates. The first plate (referred to as a "carryover plate") was designed to measure background signal, signal from positive control samples and carryover (i.e., the increase in the measured background signal associated with incomplete removal of positive calibrator beads following a measurement of positive calibrator). The plate had four columns of wells containing negative control (NC) followed by alternating columns of wells containing positive control (PC) and negative controls (see schematic below). Each column contains eight wells. Next, seven blank plates were run with air as the sample. These seven plates were equivalent to running seven plates of the negative control since the flow cell was washed with TPA Assay Buffer prior to each attempted inducement of ECL. One flow cell could run a total of 16 plates (1536 wells) in one day with this protocol.

| | Column | | | | | | | | | | | |
|---|---|---|---|---|---|---|---|---|---|---|---|---|
| Row | 1 | 2 | 3 | 4 | 5 | 6 | 7 | 8 | 9 | 10 | 11 | 12 |
| | NC | NC | NC | NC | PC | NC | PC | NC | PC | NC | PC | NC |

Additional tests were run on a M-SERIES® M8 Analyzer (IGEN International, Inc.) that ran 8 flow cells in parallel: four flow cells having Pt electrodes and four flow cells having Pt-10% Ir electrodes. This pilot study consisting of 13 stacks of 76 plates (about 12,000 samples) that comprised "carryover" plates but also included some plates designed to test the effect of sample matrices on the electrodes and to test the effect of the electrodes on the performance of an assay.

The behavior of positive control beads in the presence of different matrices (including human serum and DMSO) was studied. Matrix effects were studied for 1:4 dilutions of the matrix by pipetting 150 μl of PC and 50 μl of matrix into each well. In these experiments, the sample volume drawn into the flow cell was 150 μl.

In addition, the sensitivity of ECL measurements on the different electrodes was determined by running assays for prostate specific antigen (PSA) using PSA calibrators covering 2.5 orders of magnitude of concentration. The PSA assays used a sandwich immunoassay format that employed the following reagents from the Elecsys PSA Assay Kit (Roche Diagnostics): a biotin-labeled capture antibody, an ORI-TAG labeled detection antibody and streptavidin-coated magnetizable particles as the solid phase. The PSA assay was run analogously to the Elecsys protocol detailed in the kit's product insert.

Finally, an accelerated decontamination test was run that consisted of decontaminating the flow cells with a 25% solution of 5.25% sodium hypochlorite after every carryover plate.

B. Electrode Performance: The average ECL signal obtained with PC beads on the Ir electrode was only about 3 times the background signal. Presumably, the low signal resulted from the very small separation in the oxidation potentials for TPA and water on the Ir electrode. Applicants hypothesize that oxygen or another product of water oxidation may interfere with the generation of ECL. Despite the presence of Ir in the metal alloy, Pt-10% Ir electrodes performed similarly to Pt electrodes in terms of signal and signal to background (the mean signal obtained using PC beads was about 10% higher with Pt-10% Ir but there was overlap between the distributions of the measured signals). The electrochemical currents measured during sample excitation were comparable for the two materials.

The two materials each showed identical decreases in signal when the electrodes were exposed to serum or DMSO; the signal suppression corresponded to lower currents during the sample excitation. The signals and detection limits observed for the PSA assays were comparable for the two materials.

There was a gradual decrease in, sensitivity over time with Pt electrodes; the sensitivity for Pt—Ir electrodes was unchanged over the course of the study.

Figure 4A:
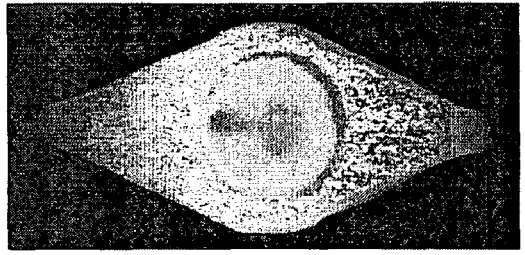
FIGS. 4A-4F are photographs of electrodes from ECL flow cells illustrating the effects of electrode etching.
Figure 4D:
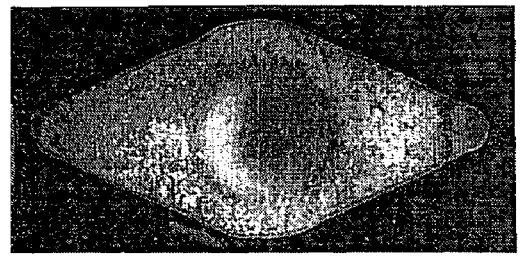
Figure 4B:
Figure 4E:
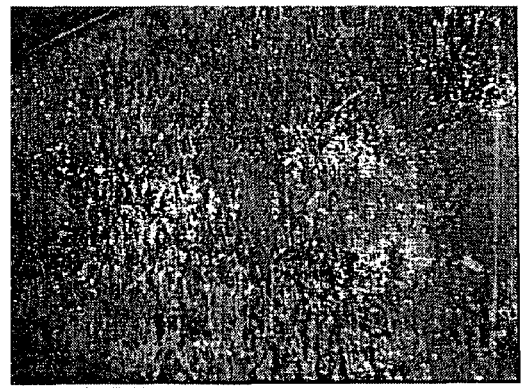
Figure 4C:
Figure 4F:
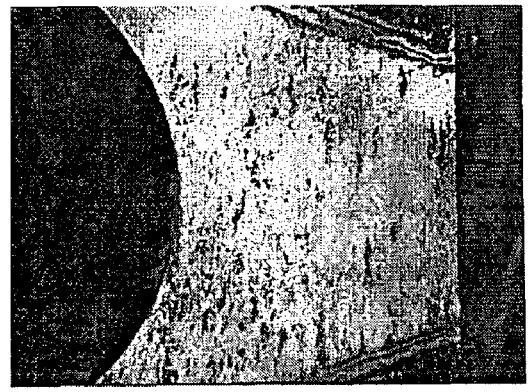

C. Resistance Of The Electrodes To Etching: FIGS. 4A-4F show photographs of the Pt and Pt—Ir electrodes after the 100 plate study (approximately 10,000 measurements). Photographs are shown for platinum (FIGS. 4A-4C) and Pt-10% Ir (FIGS. 4D-4F) electrodes. Prior to the study both electrodes were optically smooth. The Pt working electrode (FIGS. 4A and 4B) and counter electrode (FIG. 4C) were both etched more than the corresponding Pt—Ir working electrode (FIGS. 4D and 4E) and counter electrode (FIG. 4F). Photographs include pictures of the whole working electrode surfaces (FIGS. 4A and 4D), magnified pictures of the working electrode region under the counter electrode on the inlet side of the flow cell (FIGS. 4B and 4E) and magnified pictures of the counter electrode on the outlet side of the flow cell (FIGS. 4C and 4F). The four parallel bars in FIG. 4C are not part of the counter electrode but show a brass shield (for the light detector) on the cell chamber wall.

Comparison of the photographs reveal that the etching was much more severe on the counter electrodes than on the working electrodes. The etching on the working electrodes was most severe in the regions under the counter electrode. It is believed that such disparity in etching is due to non-uniformity in the current distribution during the cleaning cycle.

Waste solution from the cleaning cycle was collected and the levels of Pt and Ir were measured by atomic absorbance (AA). The Pt and Ir concentrations for the flow cell with the Pt—Ir electrodes were 60 ppb and 0.2 ppb respectively. Previous work has shown that the Pt concentration from Pt flow cells is in the 200-300 ppb range, confirming that the Pt electrode was etched to a greater extent (by a factor of 3 to 5) than the Pt-0% Ir electrode. By way of confirmation, profilometry studies have also shown that Pt electrodes show both greater loss of material as well as higher root mean square (RMS) roughness after the measurement of 12,000 samples.

Figure 5:
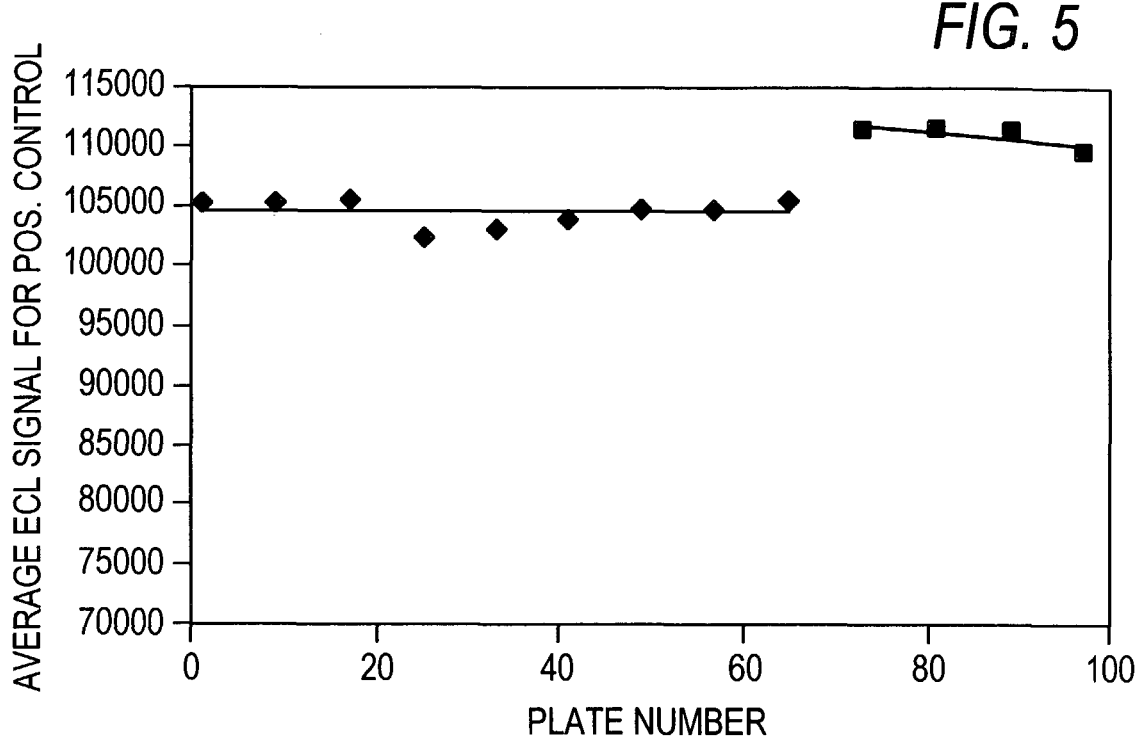
FIG. 5 is a graph showing ECL signal drift in a flow cell having a Pt-10% Ir electrode.
Figure 6:
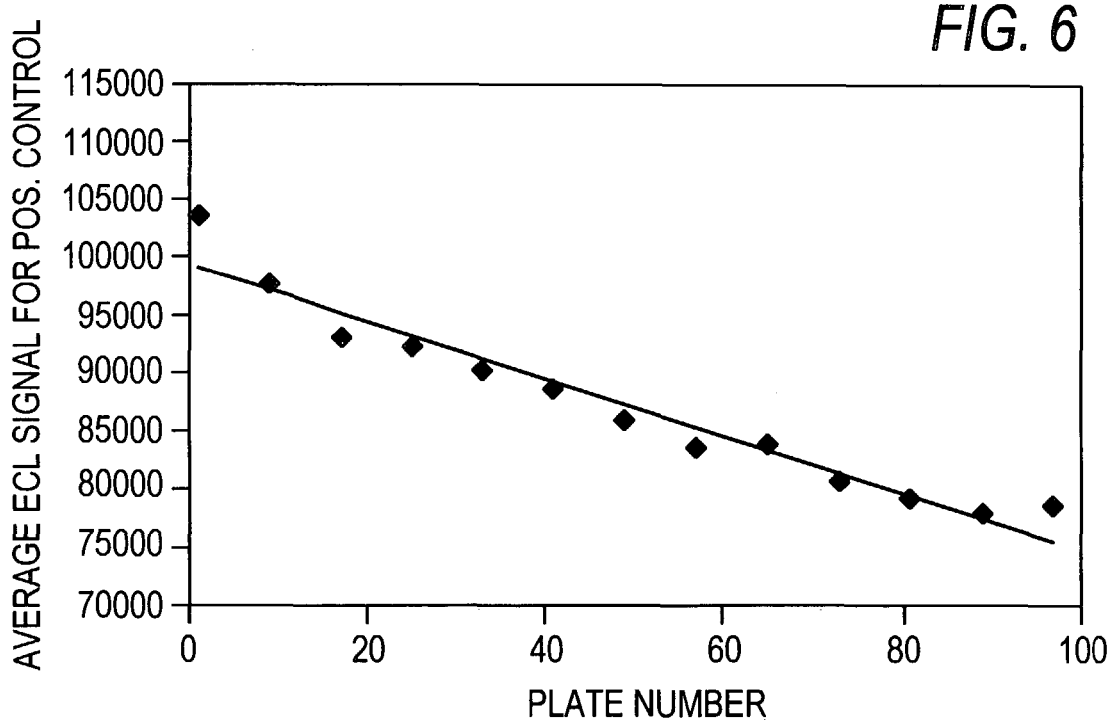
FIG. 6 is a graph showing ECL signal drift in a flow cell having a Pt electrode.

D. The Effect of Electrode Composition on ECL Signal Drift: FIGS. 5 and 6 show, respectively, the drift in average ECL signal for positive control measured in the 100 plate study of Pt—Ir and Pt electrodes (the points represent average positive control signals on the "carryover" plates). The drift with Pt—Ir electrodes (FIG. 5) was a factor of 3 less than with Pt (FIG. 6). In both Figures, a similar effect was observed when comparing the average drifts in the pilot study using the M8 instrument.

The increase in signal at plate 73 in FIG. 5 is attributed to the replacement of the TPA Assay Buffer container with a newly-opened container. The intra-plate variability (i.e., the coefficient of variance of the signal for positive calibrator) was also consistently lower with Pt—Ir electrodes.

The reduction in drift is consistent with the lower amount of etching of the Pt—Ir electrodes described in the previous section. One possible explanation for such drift is that platinum released from the counter electrode deposits on the acrylic optical window through which light is collected. Over time, this deposit results in clouding of the optical window and reduces light collection efficiency.

E. The Effect of Electrode Composition on Signal Carryover: Signal carryover refers to the increase in background signal in a measurement that results from the incomplete removal of ECL labels from previous runs. It generally results because of trapped beads in the fluidics upstream of the flow cell or because of incomplete cleaning of beads on the working electrode from the previous sample. It reduces the dynamic range of an assay and can also result in false positives in a clinical setting.

Carryover was measured using the "carryover plate" format. Carryover was calculated in parts per million (ppm), by subtracting the mean negative control signal in the absence of carryover (i.e., the average of the signal from columns 2-4 of the carryover plate) from the negative control signal in the presence of carryover (i.e., in a negative control well measured directly after a positive control well, e.g., columns 6, 8, 10 or 12 of the carryover plate), dividing the difference by the positive control signal, and multiplying by a million. For example, the carryover for a well in column 6 is $CO_6 = (NC_6 - NC_{mean})/PC_5 * 1e6$.

The average carryover that was observed under the experimental conditions described earlier was about a factor of 2 lower with Pt—Ir electrodes (approximately 250 ppm) when compared to Pt electrodes (approximately 500 ppm). The carryover also increased gradually for the Pt electrodes over time. The observed result is consistent with the higher root-mean-square (RMS) roughness, after use, for the Pt electrodes (1.4 µm) vs. the Pt/Ir electrodes (0.3 µm). The roughness is comparable to the bead diameter and it is thought that the uneven surface could cause additional bead traps in which beads collected resulting in the increased carryover that was observed.

Figure 7A:
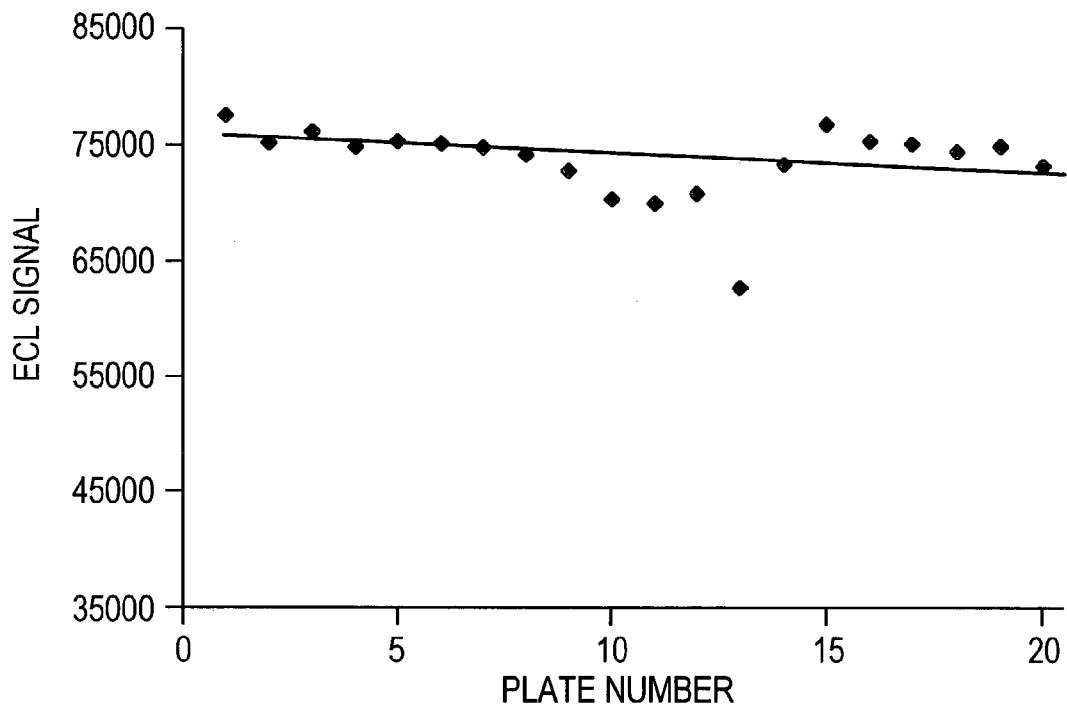
FIGS. 7A and 7B are graphs showing ECL signal drift that resulted from repeated decontamination of ECL flow cells with a 25% solution of 5.25% bleach in a flow cell having a Pt-10% Ir electrode (FIG. 7A) and in a flow cell having a Pt electrode (FIG. 7B).
Figure 7B:
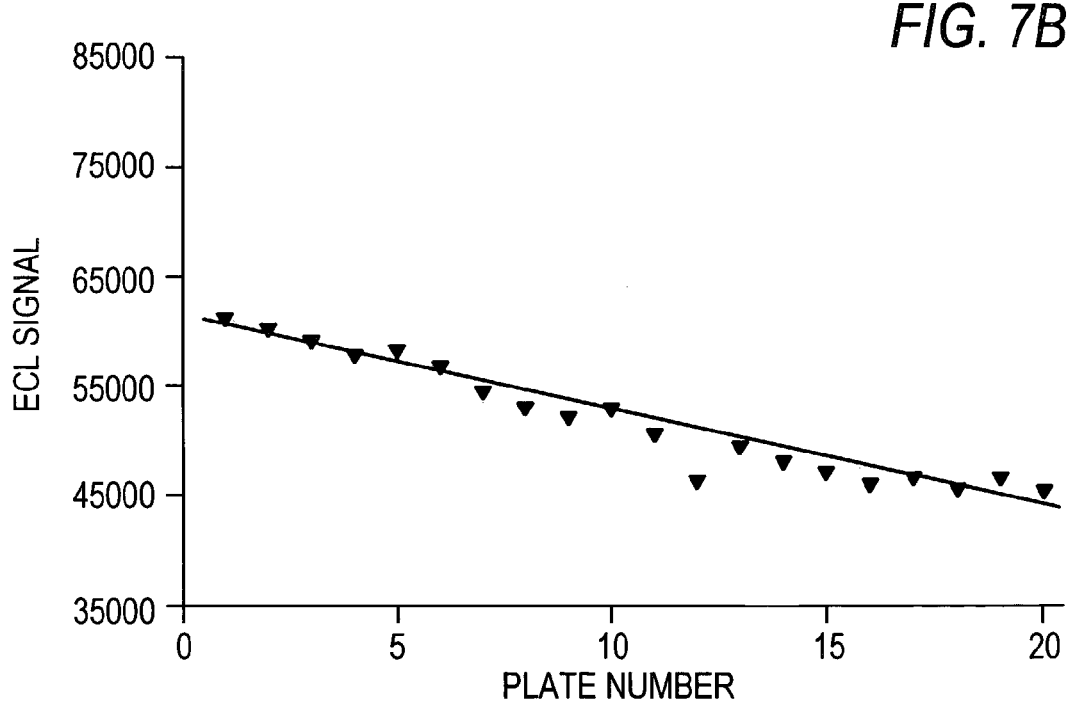

F. Effect of the Decontamination Procedure: The decontamination procedure is a maintenance procedure used to clean and sterilize the instrument fluidics. The decontamination procedure was carried out between each plate. The results of the accelerated decontamination study are shown for Pt-10% Ir (FIG. 7A) and Pt (FIG. 7B) electrodes. Each point represents an average of 12-20 positive calibrator measurements obtained using 3-5 flow cells (i.e., 4 points per flow cell per plate). From these results, it is apparent that there was a much greater drift with Pt electrodes (by about a factor of five) than with Pt—Ir electrodes, indicating that the Pt—Ir electrode was less affected by this decontamination procedure.

Example III

Comparison of ECL Measurements Using Pt and Ir Counter Electrodes

A. Methods: A study was conducted to evaluate flow cells having platinum working electrodes and iridium counter electrodes. The ECL measurements were conducted analogously to those described in Example II. The performance of the counter electrode was compared to that observed for Pt and Pt—Ir electrodes in the experiments of Example II.

Figure 8:
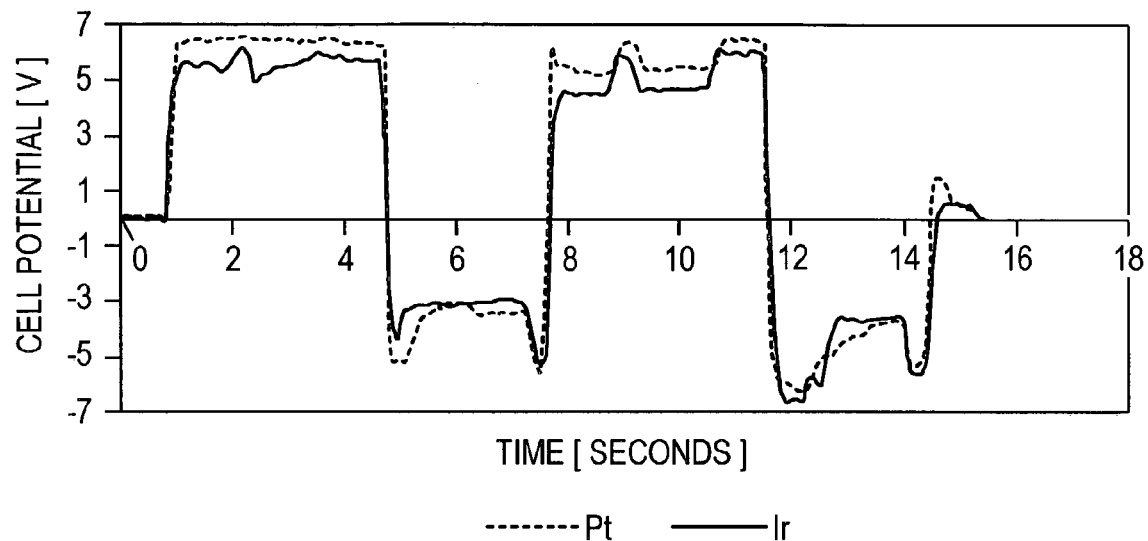
FIG. 8 is a graph of cell potentials measured during cleaning procedures in flow cells having Pt or Ir counter electrodes.

B. Counter Electrode Performance: The mean ECL signals observed for the PC and NC samples with an Ir counter electrode were comparable to those with a Pt counter electrode (within 10% of each other). FIG. 8 shows the cell potentials (i.e., the applied voltage across the working and counter electrodes) during the cleaning cycle under conditions where water oxidation to either hydrogen or oxygen occurs on the electrodes. In this figure, a positive potential reflects an oxidizing potential at the counter electrode.

In the cells with the Ir counter electrodes, the cell potential was lower by about 1 V during positive potentials and by about 0.3 V during negative potentials than the cell potential observed in cells with a platinum counter electrode.

It is believed that this reduction in cell potentials is because Ir has lower over potentials for water oxidation as compared to Pt. Rh also has lower over potentials for water oxidation relative to Pt and is expected to show similar benefits as a counter electrode for ECL. Advantageously, when these materials are used for the counter electrode, lower counter electrode potentials and cell potentials are obtained during the cleaning cycle described above. This improvement should result in reduced counter electrode etching and increased electrode lifetime.

C. Resistance of the Electrodes to Etching: After 64 plates, the mean etch depth for the Ir counter electrode was measured to be between that observed for Pt-10% Ir and Pt counter electrodes when normalized to the same number of plates (Pt—Ir: 8.8 µm, Ir: 13.8 µm, Pt: 17.9 µm). The RMS roughness for the Ir counter electrode was about 0.4 µm; this value is comparable to that observed for the Pt—Ir counter electrode and about a factor of 5 lower than for the Pt counter electrode.

Figure 9:
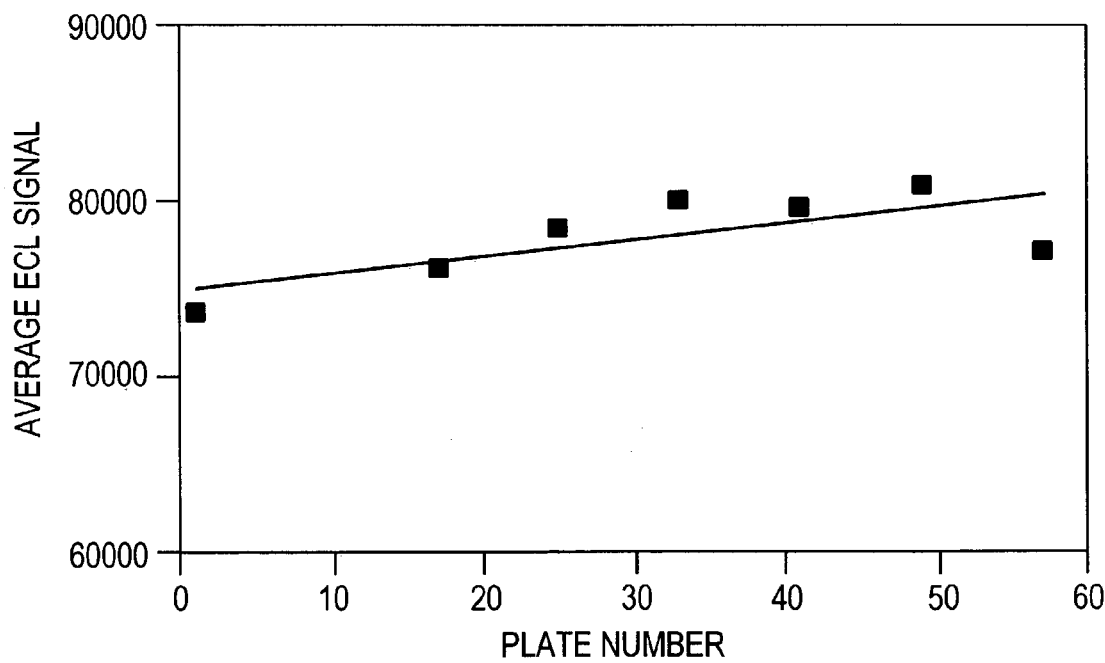
FIG. 9 is a graph showing ECL signal drift in a flow cell having a Pt working electrode and an Ir counter electrode.

D. The Effect of Counter Electrode Composition on ECL Signal Drift: FIG. 9 shows the drift of the ECL signal from positive control beads over a 64 96-well plate study utilizing an Ir counter electrode. The signal for a positive control sample is plotted as a function of the number of 96-well plates analyzed by the flow cell. The slight upward drift observed is not statistically significant. This low drift is a significant improvement over the use of a Pt counter electrode and is consistent with the reduced etching of the Ir electrodes observed. In addition, it may be that Ir oxides formed at the counter electrode remain in solution and do not deposit on the optical window, resulting in less ECL signal drift. Alternatively, the Ir oxides may be more tightly bound to the metal surface than Pt oxides and less likely to come off.

Example IV

Electrochemical Characteristics of Different Electrodes

A. Materials and Methods: Wire electrodes of different metals and alloys were obtained from Alfa Aesar (Zr, Mo, Rh, W, Re, Ir, Pt, Pt-10% Rh, Pt-20% Rh, Pt-30% Rh) and Goodfellow Corporation (Pt-8% W, Nb). All the wires were 0.01" in diameter except for the Pt and Pt-8% W wires which were 0.02" in diameter. Pt-10% Ir and Pt-30% Ir electrodes were made from 0.005" thick foils from Goodfellow Corporation. The electrodes were cleaned with acetone prior to use. The electrodes were covered with Parafilm so as to expose only the central region of the electrodes. The dimensions of the exposed region were measured with a caliper to calculate the nominal surface area. The areas varied between 20 and 30 $mm^2$.

Cyclic voltammetry (CV) tests were carried out at room temperature using a CHI Model 600A potentiostat and a BAS analytical cell with a Pt counter electrode attached to the cell top. Experiments were run in 3-electrode mode using a BAS Ag/AgCl reference electrode placed close to the electrode under test. The scan rate was 100 mV/sec. A total of 5 scan cycles were recorded, with the first and last scan in the negative (cathodic) direction. Data from the last two scans are shown and used for calculations. Electrolytes that were used include 0.3 M phosphate buffer, TPA Assay Buffer, Control Assay Buffer (a solution having the same pH and containing the same concentration of phosphate and salt as TPA Assay Buffer but lacking TPA) and free Tag (1 mM $Ru(bpy)_3Cl_2$ in phosphate buffer at the same pH as TPA Assay Buffer).

Figure 10:
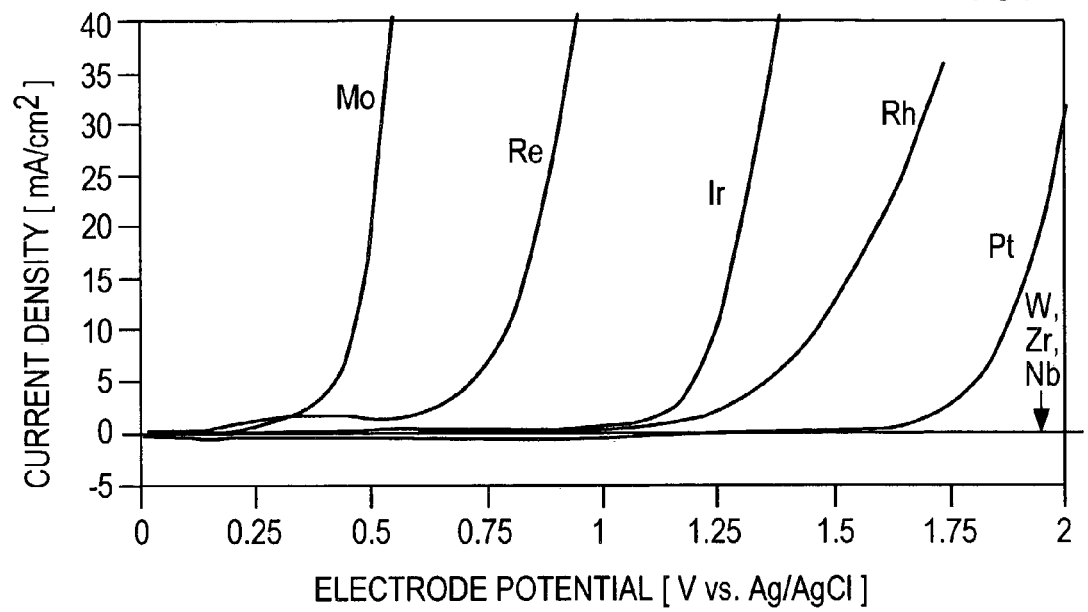
FIG. 10 is a graph in which electrochemical current is plotted as a function of the electrochemical potential at the working electrode and shows the influence of electrode composition on the oxidation of water at a pH of 6.8.

B. Water Oxidation at pH 6.8 in the Absence of TPA: FIG. 10 shows the results for water oxidation in Control Assay Buffer. Oxidizing potentials were applied to pure metal electrodes in the presence of a phosphate-buffered TPA solution at roughly neutral pH. Mo, Re and Ir have significant current densities due to water oxidation at potentials <1.3 V (the approximate potential for oxidation of ruthenium(II)-tris-bi-pyridine). In fact, Mo dissolves into solution and Re appears severely pitted. Rh, Pt, Zr, Nb and W have an electrochemical window that is wide enough for $Ru(II)(bpy)_3$ oxidation (i.e., the potential for water oxidation is significantly higher than the potential for ruthenium-tris-bipyridine). Zr, Nb and W apparently form self-passivating oxides; and the formation of oxides accounts for the very low current densities observed in FIG. 10.

Figure 11:
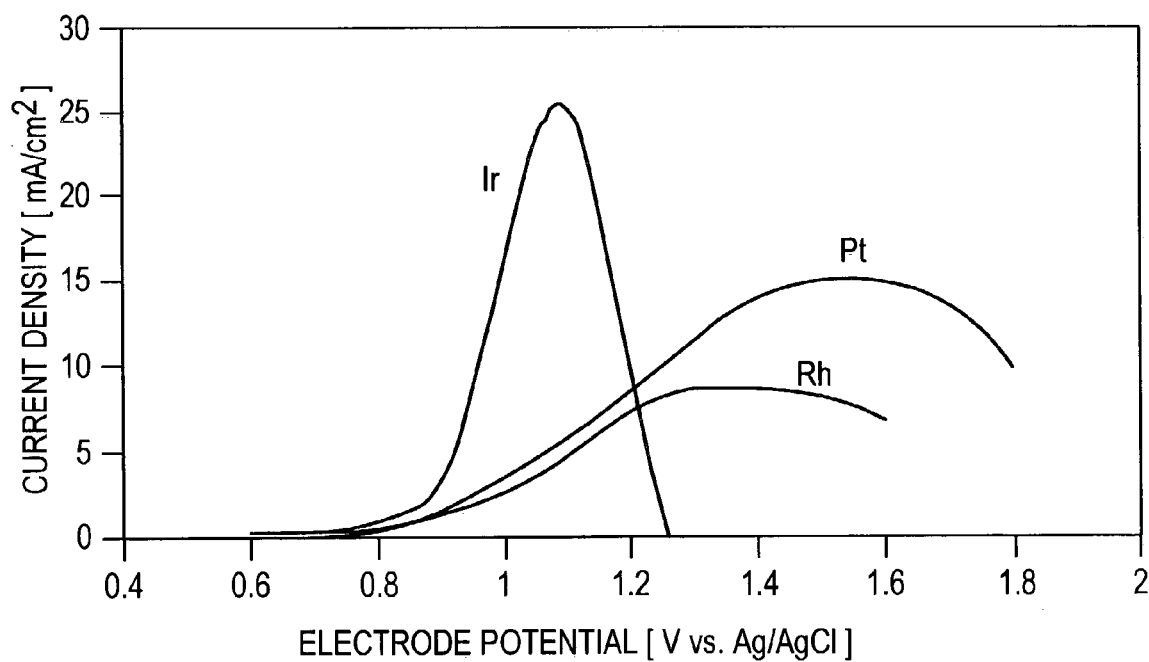
FIG. 11 is a graph in which electrochemical current is plotted as a function of the electrochemical potential at the working electrode and shows the influence of electrode composition on the oxidation of tripropylamine (TPA). Oxidizing potentials were applied at metal electrodes in the presence of a phosphate-based buffer.

C. TPA Oxidation: FIG. 11 shows the cyclic voltammetry of TPA oxidation for metals that have water oxidation at potentials >1.2V. The plots in FIG. 11 were obtained by subtraction of the currents observed for the Control Assay Buffer (i.e., in the absence of TPA) from the currents observed for TPA Assay Buffer. The figure shows that Pt was able to oxidize TPA and has an electrochemical window at approximately 1.3 V where TPA is oxidized to a greater extent than water. Applicants hypothesize these properties explain the excellent performance of Pt electrodes in generating ECL. Ir does not have such an electrochemical window. Rh has similar electrochemical properties to Pt and is expected to also be useful for generating ECL, and in particular ECL from ORI-TAG labels in the presence of TPA.

Example V

Electrochemical Characteristics of Different Alloys

Figure 12A:
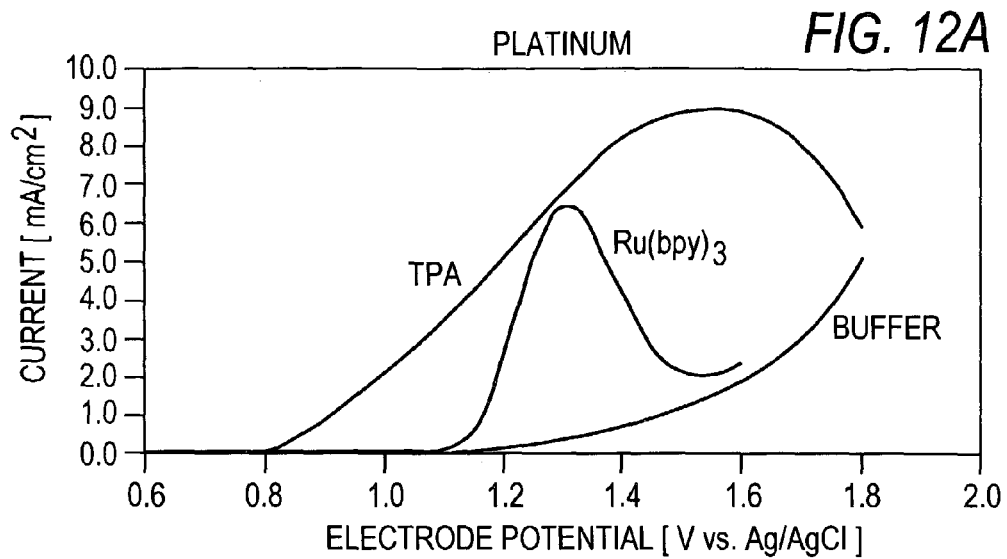
FIGS. 12A-12C are graphs of current density vs. electrode potential and illustrate the influence of Ir content on the ability of Pt alloy electrodes to oxidize phosphate-buffered water, TPA and $Ru(II)(bpy)_3$ where bpy is 2,2'-bipyridine. Results are shown for platinum (FIG. 12A), Pt-10% Ir (FIG. 12B) and Pt-30% Ir (FIG. 12C) electrodes.
Figure 12B:
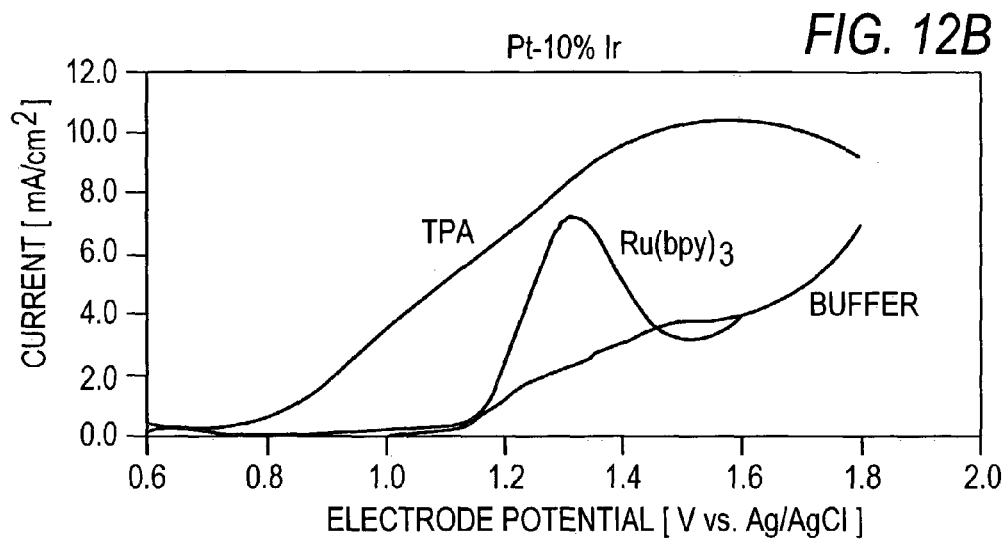
Figure 12C:
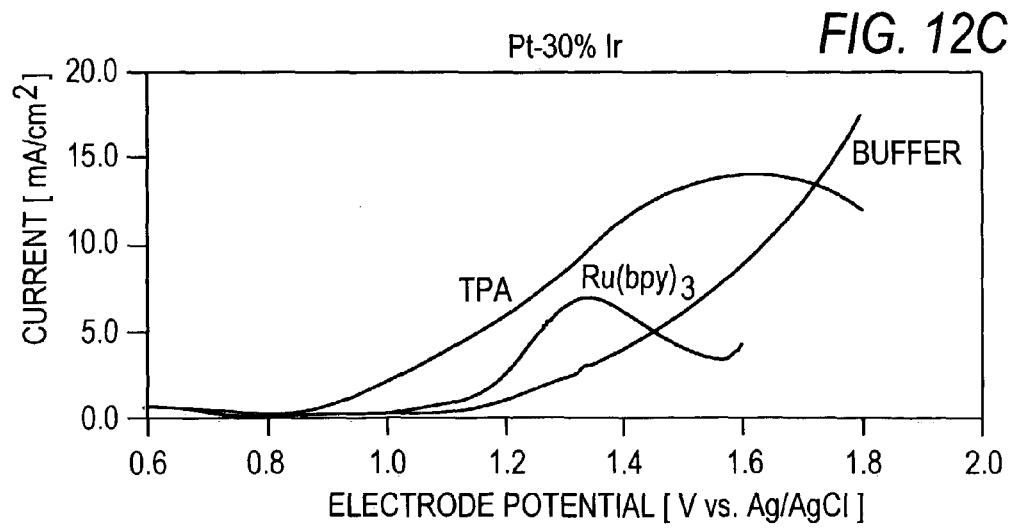
Figure 13A:
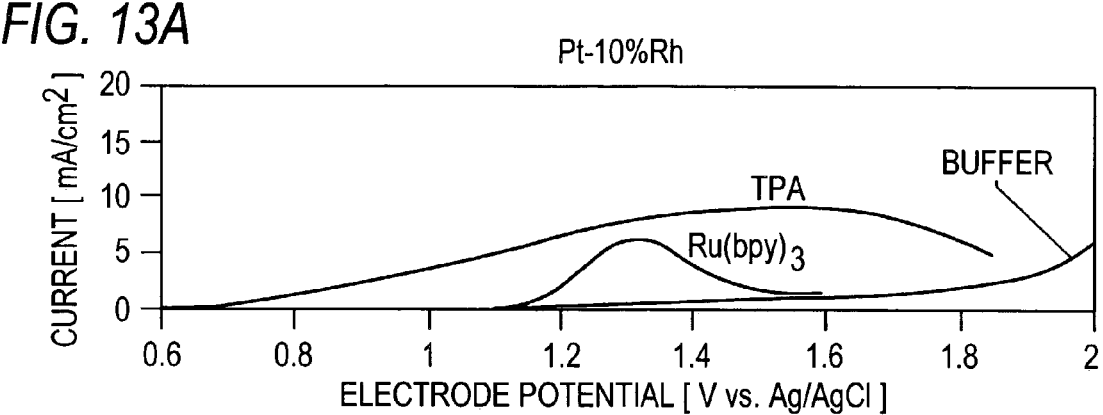
FIGS. 13A-13D are graphs of current density vs. electrode potential and illustrate the influence of Rh content on the ability of Pt alloy electrodes to oxidize phosphate-buffered water, TPA and $Ru(II)(bpy)_3$. Results are shown for Pt-10% Rh (FIG. 13A), Pt-20% Rh (FIG. 13B), Pt-30% Rh (FIG. 13C) and Rh (FIG. 13D) electrodes.
Figure 13B:
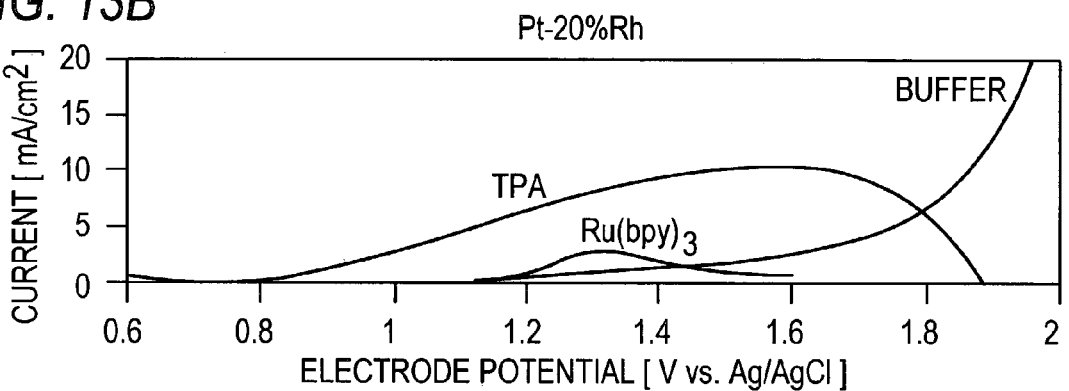
Figure 13C:
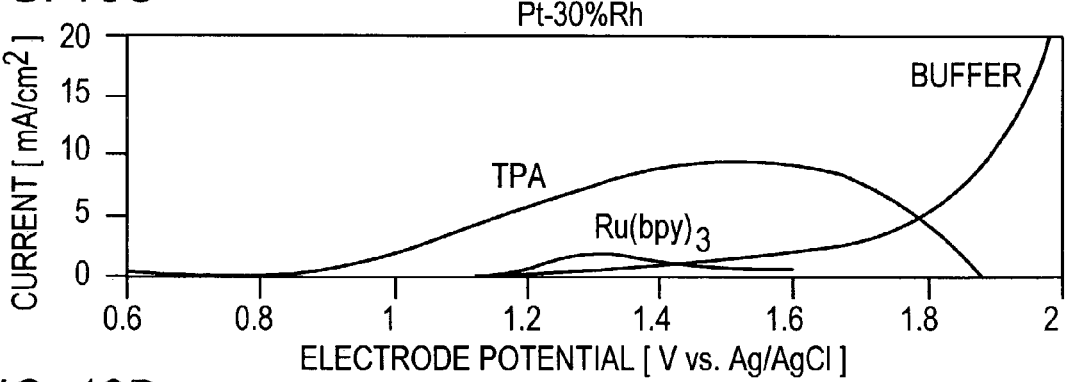
Figure 13D:
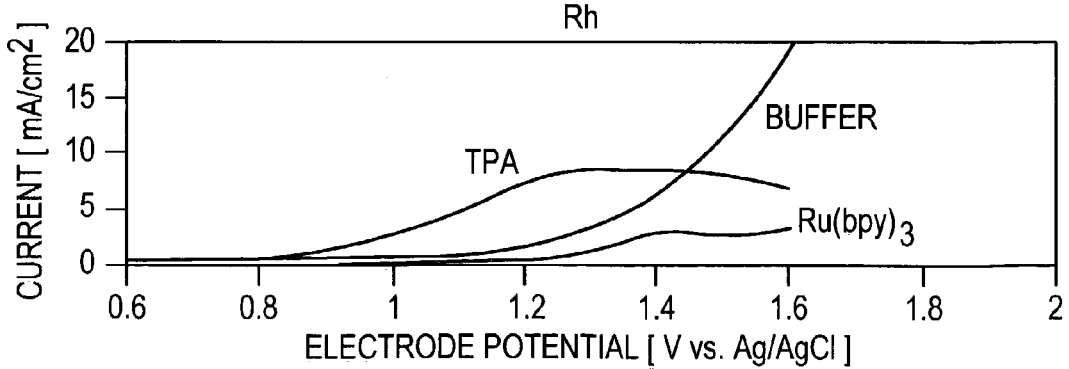

A. Oxidation of Waters TPA and $Ru(II)(bpy)_3$ (TAG) on Working Electrodes Made of Pt or Pt—Ir Alloys: FIGS. 12A-12C show the voltammetry results for the oxidation of water, TPA and $Ru(II)(bpy)_3$ on Pt (FIG. 12A), Pt-10% Ir (FIG. 12B) and Pt-30% Ir (FIG. 12C) electrodes. The behavior of the alloys is in between Pt and Ir (the I-V curves for both water and TPA lie between the curves of the pure metals as shown in FIGS. 10 and 11). Similar to Pt, there is a window of oxidizing potentials up to approximately 1.6 V or greater where TPA is oxidized to a greater extent than water, indicating that the Pt—Ir alloys with an Ir content as high as 30% are suitable electrodes for inducing ECL from $Ru(bpy)_3$ in the presence of TPA.

B. Oxidation of Water, TPA and $Ru(II)(bpy)_3$ (TAG) on Working Electrodes Made of Rh and Pt—Rh Alloys: FIGS. 13A-13D show the behavior for Pt-10% Rh (FIG. 13A), Pt-20% Rh (FIG. 13B), Pt-30% Rh (FIG. 13C) and Rh (FIG. 13D) electrodes. TPA oxidation for the Rh alloys appeared similar to Pt and higher than pure Rh. All the alloys displayed a window of oxidizing potentials up to approximately 1.6 V or greater where the current from TPA oxidation was greater than the current from water oxidation. The window for the Rh electrode extended up to 1.4 V. Thus, all the Pt—Rh and Rh electrodes that were tested are suitable electrodes for generating ECL from $Ru(bpy)_3$ in the presence of TPA.

Figure 14:
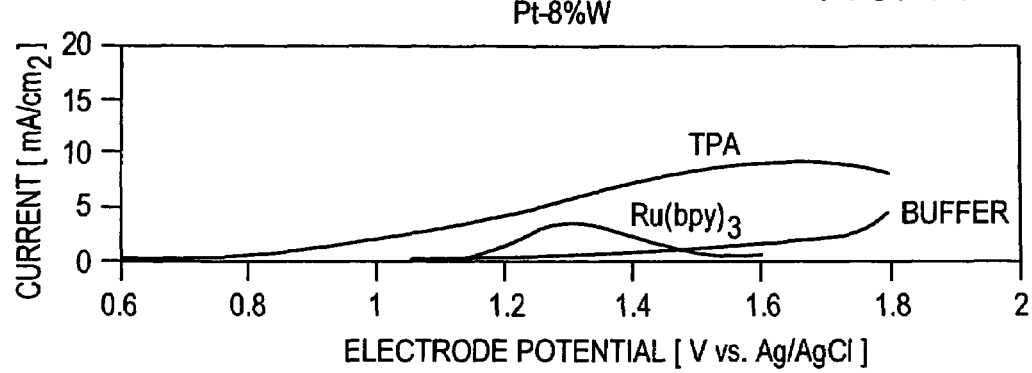
FIG. 14 is a graph of current density vs. electrode potential and illustrates the ability of a Pt-8% W alloy electrode to oxidize phosphate-buffered water, TPA and $Ru(II)(bpy)_3$.

C. Oxidation of Water, TPA and $Ru(II)(bpy)_3$ (TAG) on Working Electrodes Made of Pt—W Alloys: FIG. 14 shows the voltametric data for Pt-8% W. The alloy behavior is very similar to Pt for TPA and water oxidation and the alloy should also be suitable for ECL measurements.

Figure 15:
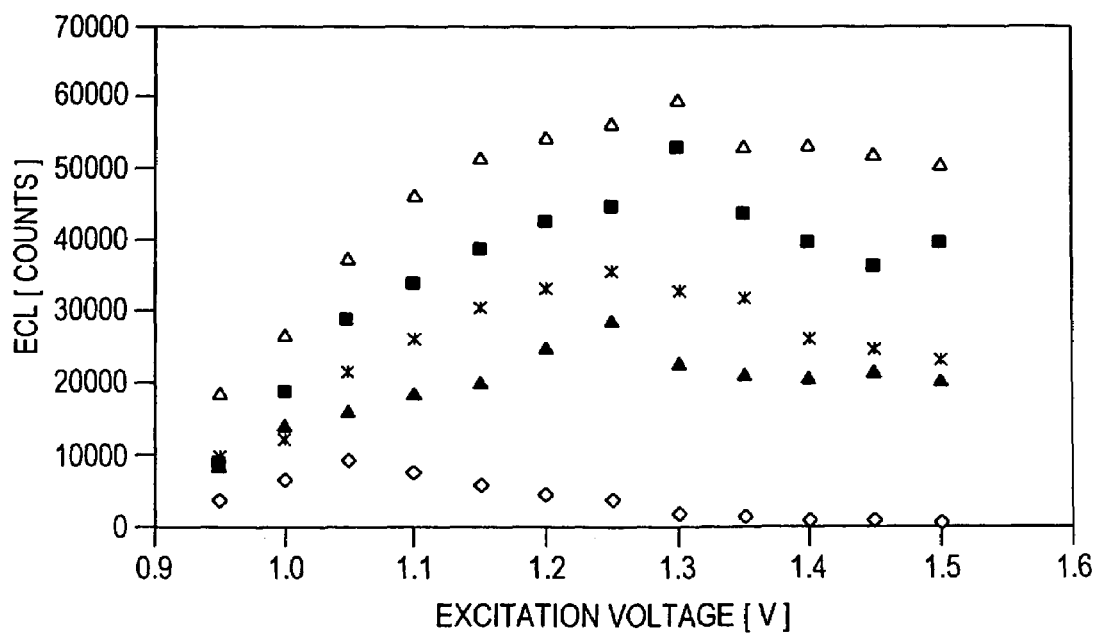
FIG. 15 is a graph showing ECL signal generated from $Ru(bpy)_3$ in TPA Assay Buffer as a function of the applied electrochemical potential at electrodes of different compositions.

D. ECL Measurements: The ability of Pt-20% Rh, Pt-10% Ir and Pt-30% Ir to act as working electrodes for ECL generation was confirmed by measuring the ECL induced at these electrodes in the presence of a 5 nM solution of free $Ru(II)(bpy)_3$ in TPA Assay Buffer. FIG. 15 shows the measured ECL as a function of the working electrode potential. Both alloys gave ECL intensities that were close to or better than those of pure Pt despite the high concentrations of Rh and Ir in the alloys. FIG. 15 also shows that, as expected, Rh was also useful as an electrode for generating ECL although the ECL intensities were somewhat lower than those observed for the other materials. The lower ECL intensities may be due to the lower currents observed on Rh electrodes for TPA and Ru(II)(bpy)$_3$ oxidation as well as the lower potential required for water oxidation.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the invention.

We claim:

1. An electrochemiluminescence cell comprising:
   a. a working electrode and a counter electrode, wherein at least one of said electrodes comprises a platinum alloy consisting essentially of:
   a first predetermined weight percent of platinum; and
   a second predetermined weight percent of iridium;
   wherein said first predetermined weight percent is from 70% to 90% and wherein said second predetermined weight percent is from 10% to 30%; and
   b. a light detector and/or a transparent portion of said cell in optical registration with said working electrode;
   wherein the counter electrode is disposed adjacent to the working electrode and the light detector and/or the transparent portion.

2. The cell of claim 1, wherein the working electrode and the counter electrode each comprise a platinum alloy consisting essentially of:
   a first predetermined weight percent of platinum; and
   a second predetermined weight percent of iridium;
   and the first predetermined weight percent is from 70% to 90% and the second predetermined weight percent is from 10% to 30%.

3. The cell of claim 1, wherein at pH in the range 6.5 to 8.0 at at least one of said electrodes, tripropylamine is oxidized at a lower potential than water.

4. The cell of claim 3, wherein at 1.3 V (vs. Ag/AgCl) the current density at at least one of said electrodes for the oxidation of tripropylamine is at least twice as large as the current density at said electrode for the oxidation of water.

5. The cell of claim 4, wherein the working electrode is for generating electrochemiluminescence.

6. The cell of claim 5, further comprising
   a support, attached to said counter electrode, having a transparent portion in optical registration with said working electrode.

7. The cell of claim 6, wherein said counter electrode comprises at least one field extending element interposed between said transparent portion and said working electrode.

8. The cell of claim 7 wherein said working electrode is capable of inducing a ruthenium-tris-bipyridine moiety to electrochemiluminesce in the presence of tripropylamine.

9. The cell of claim 8, further comprising a magnet adjacent said working electrode to collect magnetizable particles thereon.

10. The cell of claim 9, wherein said cell is a flow cell.

11. The cell of claim 10, further comprising a reference electrode.

12. The cell of claim 11, further comprising a light detector for detecting electrochemiluminescence generated in said cell.

13. The cell of claim 12, wherein said light detector is a photodiode.

14. The cell of claim 13, further comprising a source of electrical energy coupled to said electrodes.

15. The electrochemiluminescence cell of claim 14, wherein said source of electrical energy is a potentiostat.

16. The cell of claim 1, wherein the
   counter electrode comprises a field extending element and
   a support, optionally attached to said counter electrode, having a transparent portion in optical registration with said working electrode; and wherein said field extending element is interposed between said transparent portion of said support and said working electrode.

17. The cell of claim 16, wherein said field extending element traverses said transparent portion.

18. The cell of claim 16, wherein said field extending element comprises a ladder electrode.

19. The cell of claim 16, wherein said field extending element comprises projections that form an interdigitated array.

20. The cell of claim 19, wherein the current path aspect ratio is less than 2.5.

21. The cell of claim 1, further comprising
   a source of electrical energy, coupled to said electrodes, capable of maintaining said counter electrode at a substantially constant ground potential or at a potential that does not vary relative to a potential of said light detector.

22. The cell of claim 21, wherein said source of electrical energy is a potentiostat.

23. A method of conducting an electrochemiluminescence assay, the method comprising the steps of: providing an electrochemiluminescence cell, said cell comprising:
   a. a working electrode and a counter electrode, wherein at least one of said electrodes comprises a platinum alloy consisting essentially of:
   a first predetermined weight percent of platinum; and
   a second predetermined weight percent of iridium;
   wherein said first predetermined weight percent is from 70% to 90% and wherein said second predetermined weight percent is from 10% to 30%; and
   b. a light detector and/or a transparent portion of said cell in optical registration with said working electrode;
   wherein the counter electrode is disposed adjacent to the working electrode and the light detector and/or the transparent portion; and
   inducing electrochemiluminescence in the cell.

24. The method of claim 23, wherein the working electrode and the counter electrode each comprise a platinum alloy consisting essentially of:
   a first predetermined weight percent of platinum; and
   a second predetermined weight percent of iridium;
   and the first predetermined weight percent is from 70% to 90% and the second predetermined weight percent is from 10% to 30%.

25. The method of claim 24 wherein said working electrode is for generating electrochemiluminescence.

26. The method of claim 25, further comprising the steps of:
   a. forming a composition comprising an electrochemiluminescence label and an electrochemiluminescence coreactant;
   b. positioning said composition at said electrode;
   c. applying electrical energy to said electrode to induce said electrochemiluminescence label to electrochemiluminesce; and
   d. measuring an emitted electrochemiluminescence.

27. The method of claim 26, wherein said electrochemiluminescence label is an organometallic complex.

28. The method of claim 27, wherein said organometallic complex is a polypyridyl complex of Ru or Os.

29. The method of claim 27, wherein said organometallic complex comprises a ruthenium-tris-bipyridine moiety.

30. The method of claim 29, wherein said electrochemiluminescence coreactant is a molecule capable of being oxidized to produce a strong reductant.

31. The method of claim 30, wherein said electrochemiluminescence coreactant is a tertiary amine.

32. The method of claim 31, wherein said tertiary amine is tripropylamine.

33. The method of claim 32, further comprising the step of collecting a magnetizable particle on said working electrode.

34. The method of claim 33, wherein said electrochemiluminescence label is present on said magnetizable particle.

35. The method of claim 34, further comprising the step of cleaning said working electrode by applying electrical energy to said working electrode.

36. The method of claim 35, wherein electrochemiluminescence is induced within an electrochemiluminescence flow cell.

37. An electrochemiluminescence cell comprising:
a. a working electrode and a counter electrode, wherein at least one of said electrodes comprises a platinum alloy comprising:
   a first weight percent of platinum of approximately 90%; and
   a second weight percent of iridium of approximately 10%;
b. a light detector and/or a transparent portion of said cell in optical registration with said working electrode;
wherein the counter electrode is disposed adjacent to the working electrode and the light detector and/or the transparent portion.

38. An electrochemiluminescence cell comprising:
a. a working electrode and a counter electrode, wherein at least one of said electrodes comprises a platinum alloy comprising:
   a first weight percent of platinum of approximately 70%; and
   a second weight percent of iridium of approximately 30%;
b. a light detector and/or a transparent portion of said cell in optical registration with said working electrode;
wherein the counter electrode is disposed adjacent to the working electrode and the light detector and/or the transparent portion.

39. An electrochemiluminescence cell comprising:
a. a working electrode and a counter electrode, wherein at least one of said electrodes comprises a platinum alloy comprising:
   a first weight percent of platinum of approximately 80%; and
   a second weight percent of rhodium of approximately 20%;
b. a light detector and/or a transparent portion of said cell in optical registration with said working electrode;
wherein the counter electrode is disposed adjacent to the working electrode and the light detector and/or the transparent portion.

40. The cell of claim 39, further comprising a magnet adjacent said working electrode to collect magnetizable particles thereon.

41. The cell of claim 39, wherein the working electrode and the counter electrode each comprise a platinum alloy comprising a first weight percent of platinum of approximately 80% and a second weight percent of rhodium of approximately 20%.

42. The cell of claim 39, further comprising a reference electrode.

43. The cell of claim 39, wherein said light detector is a photodiode.

* * * * *

UNITED STATES PATENT AND TRADEMARK OFFICE
CERTIFICATE OF CORRECTION

| | | |
|---|---|---|
| PATENT NO. | : 7,553,448 B2 | Page 1 of 1 |
| APPLICATION NO. | : 10/600164 | |
| DATED | : June 30, 2009 | |
| INVENTOR(S) | : Kumar et al. | |

It is certified that error appears in the above-identified patent and that said Letters Patent is hereby corrected as shown below:

On the Title Page:

The first and sole Notice should read --

Subject to any disclaimer, the term of this patent is extended or adjusted under 35 U.S.C. 154(b) by 1003 days.

Signed and Sealed this

Twenty-eighth Day of September, 2010

David J. Kappos
*Director of the United States Patent and Trademark Office*